(12) United States Patent
Mathur et al.

(10) Patent No.: US 11,389,659 B2
(45) Date of Patent: *Jul. 19, 2022

(54) EXTERNAL PULSE GENERATOR DEVICE AND ASSOCIATED METHODS FOR TRIAL NERVE STIMULATION

(71) Applicant: Axonics, Inc., Irvine, CA (US)

(72) Inventors: Prabodh Mathur, Laguna Niguel, CA (US); Rinda Sama, Irvine, CA (US); Dennis Schroeder, Irvine, CA (US); Eric Schmid, Irvine, CA (US); Stuart Karten, Irvine, CA (US)

(73) Assignee: AXONICS, INC., Irvine, CA (US)

( * ) Notice: Subject to any disclaimer, the term of this patent is extended or adjusted under 35 U.S.C. 154(b) by 233 days.

This patent is subject to a terminal disclaimer.

(21) Appl. No.: 16/808,270

(22) Filed: Mar. 3, 2020

(65) Prior Publication Data

US 2020/0254267 A1 Aug. 13, 2020

Related U.S. Application Data

(63) Continuation of application No. 15/719,461, filed on Sep. 28, 2017, now Pat. No. 10,589,103, which is a (Continued)

(51) Int. Cl.
*A61N 1/37* (2006.01)
*A61N 1/372* (2006.01)
(Continued)

(52) U.S. Cl.
CPC ..... *A61N 1/37241* (2013.01); *A61N 1/36007* (2013.01); *A61N 1/36017* (2013.01);
(Continued)

(58) Field of Classification Search
None
See application file for complete search history.

(56) References Cited

U.S. PATENT DOCUMENTS 3,057,356 A 10/1962 Greatbatch
3,348,548 A 10/1967 Chardack
(Continued)

FOREIGN PATENT DOCUMENTS

AT 520440 9/2011
AU 4664800 11/2000
(Continued)

OTHER PUBLICATIONS

US 9,601,939 B2, 03/2017, Cong et al. (withdrawn)
(Continued)

*Primary Examiner* — Ankit D Tejani
(74) *Attorney, Agent, or Firm* — Kilpatrick Townsend & Stockton LLP

(57) ABSTRACT

Systems and methods for providing a trial neurostimulation to a patient for assesssing suitability of a permanently implanted neurostimulation are provided herein. In one aspect, a trial neurostimulation system includes an EPG patch adhered to a skin surface of a patient and connected to a lead extending through a percutaneous incision to a target tissue location. The EPG may be a modified version of the IPG used in the permanent system, the EPG may be smaller and/or lighter than the corresponding IPG device. The EPG and a lead extension may be sealed to allow improved patient mobility and reduced risk of infection. The EPG may be compatible with wireless systems used to control and monitor the IPG such that operation and control of the EPG is substantially the same in each system to allow seemless conversion to the permanently implanted system.

30 Claims, 9 Drawing Sheets

Related U.S. Application Data continuation of application No. 14/827,081, filed on Aug. 14, 2015, now Pat. No. 9,802,051.

(60) Provisional application No. 62/041,611, filed on Aug. 25, 2014, provisional application No. 62/038,131, filed on Aug. 15, 2014.

(51) Int. Cl.
  *A61N 1/36* (2006.01)
  *A61N 1/05* (2006.01)
  *A61N 1/375* (2006.01)

(52) U.S. Cl.
  CPC .......... *A61N 1/0551* (2013.01); *A61N 1/0558* (2013.01); *A61N 1/36107* (2013.01); *A61N 1/36132* (2013.01); *A61N 1/375* (2013.01)

(56) References Cited

U.S. PATENT DOCUMENTS

| | | |
|---|---|---|
| 3,646,940 A | 3/1972 | Timm et al. |
| 3,824,129 A | 7/1974 | Fagan, Jr. |
| 3,825,015 A | 7/1974 | Berkovits |
| 3,888,260 A | 6/1975 | Fischell |
| 3,902,501 A | 9/1975 | Citron et al. |
| 3,939,843 A | 2/1976 | Smyth |
| 3,942,535 A | 3/1976 | Schulman |
| 3,970,912 A | 7/1976 | Hoffman |
| 3,995,623 A | 12/1976 | Blake et al. |
| 4,019,518 A | 4/1977 | Maurer et al. |
| 4,044,774 A | 8/1977 | Corbin et al. |
| 4,082,097 A | 4/1978 | Mann et al. |
| 4,141,365 A | 2/1979 | Fischell et al. |
| 4,166,469 A | 9/1979 | Littleford |
| 4,269,198 A | 5/1981 | Stokes |
| 4,285,347 A | 8/1981 | Hess |
| 4,340,062 A | 7/1982 | Thompson et al. |
| 4,379,462 A | 4/1983 | Borkan et al. |
| 4,407,303 A | 10/1983 | Akerstrom |
| 4,437,475 A | 3/1984 | White |
| 4,512,351 A | 4/1985 | Pohndorf |
| 4,550,731 A | 11/1985 | Batina et al. |
| 4,558,702 A | 12/1985 | Barreras et al. |
| 4,654,880 A | 3/1987 | Sontag |
| 4,662,382 A | 5/1987 | Sluetz et al. |
| 4,719,919 A | 1/1988 | Marchosky et al. |
| 4,721,118 A | 1/1988 | Harris |
| 4,722,353 A | 2/1988 | Sluetz |
| 4,744,371 A | 5/1988 | Harris |
| 4,800,898 A | 1/1989 | Hess et al. |
| 4,848,352 A | 7/1989 | Pohndorf et al. |
| 4,860,446 A | 8/1989 | Lessar et al. |
| 4,957,118 A | 9/1990 | Erlebacher |
| 4,979,517 A | 12/1990 | Grossman et al. |
| 4,989,617 A | 2/1991 | Memberg et al. |
| 5,012,176 A | 4/1991 | Laforge |
| 5,052,407 A | 10/1991 | Hauser et al. |
| 5,197,466 A | 3/1993 | Marchosky et al. |
| 5,204,611 A | 4/1993 | Nor et al. |
| 5,255,691 A | 10/1993 | Otten |
| 5,257,634 A | 11/1993 | Kroll |
| 5,342,408 A | 8/1994 | Decoriolis et al. |
| 5,374,279 A | 12/1994 | Duffin, Jr. et al. |
| 5,386,084 A | 1/1995 | Risko |
| 5,439,485 A | 8/1995 | Mar et al. |
| 5,476,499 A | 12/1995 | Hirschberg |
| 5,484,445 A | 1/1996 | Knuth |
| 5,518,155 A | 5/1996 | Gallagher |
| 5,571,148 A | 11/1996 | Loeb et al. |
| 5,592,070 A | 1/1997 | Mino |
| 5,637,981 A | 6/1997 | Nagai et al. |
| 5,669,790 A | 9/1997 | Carson et al. |
| 5,676,162 A | 10/1997 | Larson, Jr. et al. |
| 5,690,693 A | 11/1997 | Wang et al. |
| 5,702,428 A | 12/1997 | Tippey et al. |
| 5,702,431 A | 12/1997 | Wang et al. |
| 5,712,795 A | 1/1998 | Layman et al. |
| 5,713,939 A | 2/1998 | Nedungadi et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,871,532 A | 2/1999 | Schroeppel |
| 5,876,423 A | 3/1999 | Braun |
| 5,902,331 A | 5/1999 | Bonner et al. |
| 5,948,006 A | 9/1999 | Mann |
| 5,949,632 A | 9/1999 | Barreras, Sr. et al. |
| 5,957,965 A | 9/1999 | Moumane et al. |
| 5,974,344 A | 10/1999 | Shoemaker, II et al. |
| 5,991,665 A | 11/1999 | Wang et al. |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,065,154 A | 5/2000 | Hulings et al. |
| 6,067,474 A | 5/2000 | Schulman et al. |
| 6,075,339 A | 6/2000 | Reipur et al. |
| 6,076,017 A | 6/2000 | Taylor et al. |
| 6,081,097 A | 6/2000 | Seri et al. |
| 6,083,247 A | 7/2000 | Rutten et al. |
| 6,104,957 A | 8/2000 | Alo et al. |
| 6,104,960 A | 8/2000 | Duysens et al. |
| 6,138,681 A | 10/2000 | Chen et al. |
| 6,165,180 A | 12/2000 | Cigaina et al. |
| 6,166,518 A | 12/2000 | Echarri et al. |
| 6,169,387 B1 | 1/2001 | Kaib |
| 6,172,556 B1 | 1/2001 | Prentice |
| 6,178,353 B1 | 1/2001 | Griffith et al. |
| 6,181,105 B1 | 1/2001 | Cutolo et al. |
| 6,191,365 B1 | 2/2001 | Avellanet |
| 6,208,894 B1 | 3/2001 | Schulman et al. |
| 6,212,430 B1 | 4/2001 | Kung |
| 6,212,431 B1 | 4/2001 | Hahn et al. |
| 6,221,513 B1 | 4/2001 | Lasater |
| 6,227,204 B1 | 5/2001 | Baumann et al. |
| 6,243,608 B1 | 6/2001 | Pauly et al. |
| 6,246,911 B1 | 6/2001 | Seligman |
| 6,249,703 B1 | 6/2001 | Stanton et al. |
| 6,265,789 B1 | 7/2001 | Honda et al. |
| 6,275,737 B1 | 8/2001 | Mann |
| 6,278,258 B1 | 8/2001 | Echarri et al. |
| 6,282,448 B1 | 8/2001 | Katz et al. |
| 6,305,381 B1 | 10/2001 | Weijand et al. |
| 6,306,100 B1 | 10/2001 | Prass |
| 6,315,721 B2 | 11/2001 | Schulman et al. |
| 6,316,909 B1 | 11/2001 | Honda et al. |
| 6,321,118 B1 | 11/2001 | Hahn |
| 6,327,504 B1 | 12/2001 | Dolgin et al. |
| 6,354,991 B1 | 3/2002 | Gross et al. |
| 6,360,750 B1 | 3/2002 | Gerber et al. |
| 6,381,496 B1 | 4/2002 | Meadows et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,453,198 B1 | 9/2002 | Torgerson et al. |
| 6,466,817 B1 | 10/2002 | Kaula et al. |
| 6,473,652 B1 | 10/2002 | Sarwal et al. |
| 6,500,141 B1 | 12/2002 | Irion |
| 6,505,075 B1 | 1/2003 | Weiner |
| 6,505,077 B1 | 1/2003 | Kast et al. |
| 6,510,347 B2 | 1/2003 | Borkan |
| 6,516,227 B1 | 2/2003 | Meadows et al. |
| 6,517,227 B2 | 2/2003 | Stidham et al. |
| 6,521,309 B1 | 2/2003 | Chen et al. |
| 6,542,846 B1 | 4/2003 | Miller et al. |
| 6,553,263 B1 | 4/2003 | Meadows et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,609,945 B2 | 8/2003 | Jimenez et al. |
| 6,652,449 B1 | 11/2003 | Gross et al. |
| 6,662,051 B1 | 12/2003 | Eraker et al. |

(56) References Cited

U.S. PATENT DOCUMENTS

| | | |
|---|---|---|
| 6,664,763 B2 | 12/2003 | Echarri et al. |
| 6,685,638 B1 | 2/2004 | Taylor et al. |
| 6,687,543 B1 | 2/2004 | Isaac |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,120,499 B2 | 10/2006 | Thrope et al. |
| 7,127,298 B1 | 10/2006 | He et al. |
| 7,131,996 B2 | 11/2006 | Wasserman et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,167,756 B1 | 1/2007 | Torgerson et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,239,918 B2 | 7/2007 | Strother et al. |
| 7,245,972 B2 | 7/2007 | Davis |
| 7,286,880 B2 | 10/2007 | Olson et al. |
| 7,295,878 B1 | 11/2007 | Meadows et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,444,184 B2 | 10/2008 | Boveja et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,486,048 B2 | 2/2009 | Tsukamoto et al. |
| 7,496,404 B2 | 2/2009 | Meadows et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,650,192 B2 | 1/2010 | Wahlstrand |
| 7,680,540 B2 | 3/2010 | Jensen et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,878,207 B2 | 2/2011 | Goetz et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,460 B2 | 7/2012 | Schleicher et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,382,059 B2 | 2/2013 | Le Gette et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,452,409 B2 | 5/2013 | Bachinski et al. |
| 8,457,756 B2 | 6/2013 | Rahman |

(56) References Cited

U.S. PATENT DOCUMENTS

| | | | |
|---|---|---|---|
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,544,322 B2 | 10/2013 | Minami et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,700,177 B2 | 4/2014 | Strother et al. |
| 8,706,254 B2 | 4/2014 | Vamos et al. |
| 8,725,262 B2 | 5/2014 | Olson et al. |
| 8,725,269 B2 | 5/2014 | Nolan et al. |
| 8,738,138 B2 | 5/2014 | Funderburk et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,855,767 B2 | 10/2014 | Faltys et al. |
| 8,892,217 B2 | 11/2014 | Camps et al. |
| 8,918,174 B2 | 12/2014 | Woods et al. |
| 8,938,303 B1 | 1/2015 | Matsen |
| 8,954,148 B2 | 2/2015 | Labbe et al. |
| 8,989,861 B2 | 3/2015 | Su et al. |
| 9,044,592 B2 | 6/2015 | Imran et al. |
| 9,050,473 B2 | 6/2015 | Woods et al. |
| 9,089,712 B2 | 7/2015 | Joshi et al. |
| 9,108,063 B2 | 8/2015 | Olson et al. |
| 9,144,680 B2 | 9/2015 | Kaula et al. |
| 9,149,635 B2 | 10/2015 | Denison et al. |
| 9,155,885 B2 | 10/2015 | Wei et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson et al. |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber et al. |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,320,899 B2 | 4/2016 | Parramon et al. |
| 9,333,339 B2 | 5/2016 | Weiner |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,592,389 B2 | 3/2017 | Moffitt |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,782,596 B2 | 10/2017 | Vamos et al. |
| 9,802,051 B2 * | 10/2017 | Mathur ............... A61N 1/36017 |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,849,278 B2 | 12/2017 | Spinelli et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |

(56) References Cited

U.S. PATENT DOCUMENTS

| | | | |
|---|---|---|---|
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,092,762 B2 | 9/2018 | Jiang et al. |
| 10,086,191 B2 | 10/2018 | Bonde et al. |
| 10,086,203 B2 | 10/2018 | Kaemmerer |
| 10,092,747 B2 | 10/2018 | Sharma et al. |
| 10,092,749 B2 | 10/2018 | Stevenson et al. |
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | Lebaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,195,423 B2 | 5/2019 | Jiang et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,448,889 B2 | 10/2019 | Gerber et al. |
| 10,456,574 B2 | 10/2019 | Chen et al. |
| 10,471,262 B2 | 11/2019 | Perryman et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 10,589,103 B2 * | 3/2020 | Mathur | A61N 1/36017 |
| 2002/0040185 A1 | 4/2002 | Atalar et al. |
| 2002/0051550 A1 | 5/2002 | Leysieffer |
| 2002/0051551 A1 | 5/2002 | Leysieffer et al. |
| 2002/0140399 A1 | 10/2002 | Echarri et al. |
| 2002/0143376 A1 | 10/2002 | Chinn |
| 2002/0177884 A1 | 11/2002 | Ahn et al. |
| 2003/0018369 A1 | 1/2003 | Thompson et al. |
| 2003/0114899 A1 | 6/2003 | Woods et al. |
| 2003/0120323 A1 | 6/2003 | Meadows et al. |
| 2003/0212440 A1 | 11/2003 | Boveja |
| 2004/0073265 A1 | 4/2004 | Scheiner |
| 2004/0098065 A1 | 5/2004 | Hagglof et al. |
| 2004/0098068 A1 | 5/2004 | Carbunaru et al. |
| 2004/0210290 A1 | 10/2004 | Omar-Pasha |
| 2004/0250820 A1 | 12/2004 | Forsell |
| 2004/0267137 A1 | 12/2004 | Peszynski et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1 | 4/2005 | Olson et al. |
| 2005/0075698 A1 | 4/2005 | Phillips et al. |
| 2005/0075699 A1 | 4/2005 | Olson et al. |
| 2005/0075700 A1 | 4/2005 | Schommer et al. |
| 2005/0104577 A1 | 5/2005 | Matei et al. |
| 2005/0187590 A1 | 8/2005 | Boveja et al. |
| 2006/0041283 A1 | 2/2006 | Gelfand et al. |
| 2006/0142822 A1 | 6/2006 | Tulgar |
| 2006/0149345 A1 | 7/2006 | Boggs et al. |
| 2006/0200205 A1 | 9/2006 | Haller |
| 2006/0206166 A1 | 9/2006 | Weiner |
| 2007/0027494 A1 | 2/2007 | Gerber |
| 2007/0027501 A1 | 2/2007 | Jensen |
| 2007/0032836 A1 | 2/2007 | Thrope et al. |
| 2007/0060980 A1 | 3/2007 | Strother et al. |
| 2007/0060991 A1 | 3/2007 | North et al. |
| 2007/0123952 A1 | 5/2007 | Strother et al. |
| 2007/0213795 A1 | 9/2007 | Bradley et al. |
| 2007/0239224 A1 | 10/2007 | Bennett et al. |
| 2007/0265675 A1 | 11/2007 | Lund et al. |
| 2007/0293914 A1 | 12/2007 | Woods et al. |
| 2008/0065182 A1 | 3/2008 | Strother et al. |
| 2008/0132969 A1 | 6/2008 | Bennett et al. |
| 2008/0154179 A1 | 6/2008 | Cantor et al. |
| 2008/0154335 A1 | 6/2008 | Thrope et al. |
| 2008/0161874 A1 | 7/2008 | Bennett et al. |
| 2008/0183236 A1 | 7/2008 | Gerber |
| 2008/0292685 A1 | 11/2008 | Wang et al. |
| 2009/0054952 A1 | 2/2009 | Glukhovsky et al. |
| 2009/0182216 A1 | 7/2009 | Roushey et al. |
| 2009/0198306 A1 | 8/2009 | Goetz et al. |
| 2010/0036445 A1 | 2/2010 | Sakai et al. |
| 2010/0072334 A1 | 3/2010 | Le Gette et al. |
| 2010/0076254 A1 | 3/2010 | Jimenez et al. |
| 2010/0076534 A1 | 3/2010 | Mock |
| 2010/0100158 A1 | 4/2010 | Thrope et al. |
| 2010/0106204 A1 | 4/2010 | Moffit et al. |
| 2010/0179618 A1 | 7/2010 | Marnfeldt et al. |
| 2010/0198044 A1 | 8/2010 | Gehman et al. |
| 2010/0324620 A1 | 12/2010 | Libbus et al. |
| 2011/0125214 A1 | 5/2011 | Goetz et al. |
| 2011/0152987 A1 | 6/2011 | Wahlgren et al. |
| 2011/0208123 A1 | 8/2011 | Gray et al. |
| 2011/0251662 A1 | 10/2011 | Griswold et al. |
| 2011/0257701 A1 | 10/2011 | Strother et al. |
| 2011/0270068 A1 | 11/2011 | Mehdizadeh et al. |
| 2011/0282416 A1 | 11/2011 | Hamann et al. |
| 2011/0301667 A1 | 12/2011 | Olson et al. |
| 2012/0041512 A1 | 2/2012 | Weiner |
| 2012/0046712 A1 | 2/2012 | Woods et al. |
| 2012/0123496 A1 | 5/2012 | Schotzko et al. |
| 2012/0130448 A1 | 5/2012 | Woods et al. |
| 2012/0276854 A1 | 11/2012 | Joshi et al. |
| 2012/0276856 A1 | 11/2012 | Joshi et al. |
| 2012/0290055 A1 | 11/2012 | Boggs, II |
| 2013/0004925 A1 | 1/2013 | Labbe et al. |
| 2013/0006325 A1 | 1/2013 | Woods et al. |
| 2013/0006330 A1 | 1/2013 | Wilder et al. |
| 2013/0006331 A1 | 1/2013 | Weisgarber et al. |
| 2013/0096641 A1 | 4/2013 | Strother et al. |
| 2013/0116751 A1 | 5/2013 | Moffitt et al. |
| 2013/0150925 A1 | 6/2013 | Vamos et al. |
| 2013/0172956 A1 | 7/2013 | Goddard et al. |
| 2013/0197608 A1 | 8/2013 | Eiger |
| 2013/0207863 A1 | 8/2013 | Joshi |
| 2013/0310894 A1 | 11/2013 | Trier |
| 2013/0325097 A1 | 12/2013 | Loest |
| 2013/0331909 A1 * | 12/2013 | Gerber | A61N 1/36007 607/59 |
| 2014/0025137 A1 | 1/2014 | Meskens |

(56) References Cited

U.S. PATENT DOCUMENTS

| | | |
|---|---|---|
| 2014/0194948 A1 | 7/2014 | Strother et al. |
| 2014/0222112 A1 | 8/2014 | Fell |
| 2014/0237806 A1 | 8/2014 | Smith et al. |
| 2014/0277270 A1 | 9/2014 | Parramon et al. |
| 2015/0028798 A1 | 1/2015 | Dearden et al. |
| 2015/0088227 A1 | 3/2015 | Shishilla et al. |
| 2015/0094790 A1 | 4/2015 | Shishilla et al. |
| 2015/0100106 A1 | 4/2015 | Shishilla et al. |
| 2015/0214604 A1 | 7/2015 | Zhao et al. |
| 2015/0231402 A1 | 8/2015 | Aghassian |
| 2016/0045745 A1 | 2/2016 | Mathur et al. |
| 2017/0197079 A1 | 7/2017 | Illegems et al. |
| 2017/0340878 A1 | 11/2017 | Wahlstrand et al. |
| 2018/0021587 A1 | 1/2018 | Strother et al. |
| 2018/0036477 A1 | 2/2018 | Olson et al. |
| 2018/0117344 A1 | 5/2018 | Mathur et al. |
| 2019/0269918 A1 | 9/2019 | Parker |
| 2019/0351244 A1 | 11/2019 | Shishilla et al. |
| 2019/0358395 A1 | 11/2019 | Olson et al. |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CN | 1745857 | 3/2006 |
| CN | 101252969 A | 8/2008 |
| CN | 102176945 | 9/2011 |
| CN | 102921105 A | 2/2013 |
| CN | 203280903 U | 11/2013 |
| CN | 103638599 A | 3/2014 |
| CN | 107148294 | 9/2017 |
| DE | 3146182 | 6/1983 |
| EP | 0656218 | 6/1995 |
| EP | 1205004 | 5/2002 |
| EP | 1680182 | 7/2006 |
| EP | 2243509 | 10/2010 |
| EP | 1680182 | 5/2013 |
| EP | 3180071 | 6/2017 |
| ES | 2395128 | 2/2013 |
| HK | 1098715 | 3/2012 |
| JP | 2005261662 | 9/2005 |
| JP | 2007268293 | 10/2007 |
| JP | 4125357 | 7/2008 |
| JP | 2008525089 | 7/2008 |
| JP | 2011529718 | 12/2011 |
| JP | 2017523867 | 8/2017 |
| WO | 9820933 | 5/1998 |
| WO | 9918879 | 4/1999 |
| WO | 9934870 | 7/1999 |
| WO | 9942173 | 8/1999 |
| WO | 0056677 | 9/2000 |
| WO | 0065682 | 11/2000 |
| WO | 0069012 | 11/2000 |
| WO | 0183029 | 11/2001 |
| WO | 0209808 | 2/2002 |
| WO | 2004021876 | 3/2004 |
| WO | 2004103465 | 12/2004 |
| WO | 2005079295 | 9/2005 |
| WO | 2005081740 | 9/2005 |
| WO | 2007136694 | 11/2007 |
| WO | 2008021524 | 2/2008 |
| WO | 2011059565 | 5/2011 |
| WO | 2013162709 | 10/2013 |
| WO | 2014087337 | 6/2014 |
| WO | 2014151160 | 9/2014 |
| WO | 2016025909 | 2/2016 |

OTHER PUBLICATIONS

"Bu-802a: How Does Rising Internal Resistance Affect Performance? Understanding the Importance of Low Conductivity", BatteryUniversity.com, Available Online at https://batteryuniversity.com/learn/article/rising_internal_resistance, Accessed from Internet on: May 15, 2020, 10 pages.

"DOE Handbook: Primer on Lead-Acid Storage Batteries", U.S. Dept. of Energy, Available Online at: htt12s://www.stan dards.doe.gov/standards- documents/I 000/1084-bhdbk-1995/@@images/file, Sep. 1995, 54 pages.

"Medical Electrical Equipment—Part 1: General Requirements for Safety", British Standard, BS EN 60601-1:1990-BS5724-1:1989, Mar. 1979, 200 pages.

"Summary of Safety and Effectiveness", Medtronic InterStim System for Urinary Control, Apr. 15, 1999, pp. 1-18.

"The Advanced Bionics PRECISION™ Spinal Cord Stimulator System", Advanced Bionics Corporation, Apr. 27, 2004, pp. 1-18.

"UL Standard for Safety for Medical and Dental Equipment", UL 544, 4th edition, Dec. 30, 1998, 128 pages.

Barnhart et al., "A Fixed-Rate Rechargeable Cardiac Pacemaker", APL Technical Digest, Jan.-Feb. 1970, pp. 2-9.

Benditt et al., "A Combined Atrial/Ventricular Lead for Permanent Dual-Chamber Cardiac Pacing Applications", Chest, vol. 83, No. 6, Jun. 1983, pp. 929-931.

Bosch et al., "Sacral (S3) Segmental Nerve Stimulation as a Treatment for Urge Incontinence in Patients with Detrusor Instability: Results of Chronic Electrical Stimulation Using an Implantable Neural Prosthesis", The Journal of Urology, vol. 154, No. 2, Aug. 1995, pp. 504-507.

Boyce et al., "Research Related to the Development of an Artificial Electrical Stimulator for the Paralyzed Human Bladder: a Review", The Journal of Urology, vol. 91, No. 1, Jan. 1964, pp. 41-51.

Bradley et al., "Further Experience With the Radio Transmitter Receiver Unit for the Neurogenic Bladder", Journal of Neurosurgery, vol. 20, No. 11, Nov. 1963, pp. 953-960.

Broggi et al., "Electrical Stimulation of the Gasserian Ganglion for Facial Pain: Preliminary Results", Acta Neurochirurgica, vol. 39, 1987, pp. 144-146.

Cameron et al., "Effects of Posture on Stimulation Parameters in Spinal Cord Stimulation", Neuromodulation, vol. 1, No. 4, Oct. 1998, pp. 177-183.

Connelly et al., "Atrial Pacing Leads Following Open Heart Surgery: Active or Passive Fixation?", Pacing and Clinical Electrophysiology, vol. 20, No. 10, Oct. 1997, pp. 2429-2433.

Fischell, "The Development of Implantable Medical Devices at the Applied Physics Laboratory", Johns Hopkins APL Technical Digest, vol. 13 No. 1, 1992, pp. 233-243.

Gaunt et al., "Control of Urinary Bladder Function With Devices: Successes and Failures", Progress in Brain Research, vol. 152, 2006, pp. 1-24.

Ghovanloo et al., "A Small Size Large Voltage Compliance Programmable Current Source for Biomedical Implantable Microstimulators", Proceedings of the 25th Annual International Conference of the IEEE EMBS, Sep. 17-21, 2003, pp. 1979-1982.

Helland, "Technical Improvements to be Achieved by the Year 2000: Leads and Connector Technology", Rate Adaptive Cardiac Pacing, Springer Verlag, 1993, pp. 279-292.

Hidefjall, "The Pace of Innovation—Patterns of Innovation in the Cardiac Pacemaker Industry", Linkoping University Press, 1997, 398 pages.

Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.

Jonas et al., "Studies on the Feasibility of Urinary Bladder Evacuation by Direct Spinal Cord Stimulation. I. Parameters of Most Effective Stimulation", Investigative urology, vol. 13, No. 2, 1975, pp. 142-150.

Kakuta et al., "In Vivo Long Lerm Evaluation of Transcutaneous Energy Transmission for Totally Implantable Artificial Heart", ASAIO Journal, Mar.-Apr. 2000, pp. 1-2.

Kester et al., "Voltage-to-Frequency Converters", Available Online at: https://www.analog.com/media/cn/training-seminars/tutorials/ML-028.pdf, 7 pages.

(56) References Cited

OTHER PUBLICATIONS

Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.
Lewis et al., "Early Clinical Experience with the Rechargeable Cardiac Pacemaker", The Annals of Thoracic Surgery, vol. 18, No. 5, Nov. 1974, pp. 490-493.
Love et al., "Experimental Testing of a Permanent Rechargeable Cardiac Pacemaker", The Annals of Thoracic Surgery, vol. 17, No. 2, Feb. 1, 1974, pp. 152-156.
Love , "Pacemaker Troubleshooting and Follow-up", Clinical Cardiac Pacing, Defibrillation, and Resynchronization Therapy, Chapter 24, 2007, pp. 1005-1062.
Madigan et al., "Difficulty of Extraction of Chronically Implanted Tined Ventricular Endocardial Leads", Journal of the American College of Cardiology, vol. 3, No. 3, Mar. 1984, pp. 724-731.
Meglio , "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.
Meyerson , "Alleviation of Atypical Trigeminal Pain by Stimulation of the Gasserian Ganglion via an Implanted Electrode", Acta Neurochirurgica Supplementum , vol. 30, 1980, pp. 303-309.
Mitamura et al., "Development of Transcutaneous Energy Transmission System", Available Online at https://www.researchgate.net/publication/312810915 Ch.28, Jan. 1988, pp. 265-270.
Nakamura et al., "Biocompatibility and Practicality Evaluations of Transcutaneous Energy Transmission Unit for the Totally Implantable Artifical Heart System", Journal of Artificial Organs, vol. 27, No. 2, 1998, pp. 347-351.
Nashold et al., "Electromicturition in Paraplegia. Implantation of a Spinal Neuroprosthesis", Arch Surg., vol. 104, Feb. 1972, pp. 195-202.
Painter et al., "Implantation of an Endocardial Tined Lead to Prevent Early Dislodgement", The Journal of Thoracic and Cardiovascular Surgery, vol. 77, No. 2, Feb. 1979, pp. 249-251.
Perez , "Lead-Acid Battery State of Charge vs. Voltage", Available Online at http://www.rencobattery.com/resources/SOC vs-Voltage.pdf, Aug.-Sep. 1993, 5 pages.
Schaldach et al., "A Long-Lived, Reliable, Rechargeable Cardiac Pacemaker", Engineering in Medicine, vol. 1: Advances in Pacemaker Technology, 1975, 34 pages.
Scheuer-Leeser et al., "Polyurethane Leads: Facts and Controversy", PACE, vol. 6, Mar.-Apr. 1983, pp. 454-458.
Smith , "Changing Standards for Medical Equipment", UL 544 and UL 187 vs. UL 2601 ("Smith"), 2002, 8 pages.
Tanagho et al., "Bladder Pacemaker: Scientific Basis and Clinical Future", Urology, vol. 20, No. 6, Dec. 1982, pp. 614-619.
Tanagho , "Neuromodulation and Neurostimulation: Overview and Future Potential", Translational Androl Urol, vol. 1, No. 1, 2012, pp. 44-49.
Torres et al., "Electrostatic Energy-Harvesting and Battery-Charging CMOS System Prototype", Available Online at http://rincon mora.gatech.edu/12ublicat/jrnls/tcasi09_hrv_sys.pdf, pp. 1-10.
Young , "Electrical Stimulation of the Trigeminal Nerve Root for the Treatment of Chronic Facial Pain", Journal of Neurosurgery, vol. 83, No. 1, Jul. 1995, pp. 72-78.
U.S. Appl. No. 14/827,074, filed Aug. 14, 2015.
U.S. Appl. No. 14/991,649, filed Jan. 8, 2016.
U.S. Appl. No. 14/827,108, filed Aug. 14, 2015.
U.S. Appl. No. 14/991,752, filed Jan. 8, 2016.
U.S. Appl. No. 14/827,095, filed Aug. 14, 2015.
U.S. Appl. No. 14/827,067, filed Aug. 14, 2015.
U.S. Appl. No. 14/991,784, filed Jan. 8, 2016.
U.S. Appl. No. 62/101,888, filed Jan. 9, 2015.
U.S. Appl. No. 62/101,899, filed Jan. 9, 2015.
U.S. Appl. No. 62/101,897, filed Jan. 9, 2015.
U.S. Appl. No. 62/110,274, filed Jan. 30, 2015.
U.S. Appl. No. 62/038,122, filed Aug. 15, 2014.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.
U.S. Appl. No. 62/191,134, filed Jul. 10, 2015.
Elterman, "The novel Axonics® rechargeable sacral neuromodulation system: Procedural and technical impressions from an initial North American experience", Neurourology and Urodynamics, Jan. 16, 2018, pp. 1-8.
Medtronic, Controller for InterStim® Therapy, Clinician Programming Guide, purporting to bear a copyright date of 2012, 72 pages.
Medtronic, Controller Patient Programming Manual for Test Stimulation, purporting to bear a copyright date of 2012, 88 pages.
Medtronic, Interstim Icon™, Model 3037 Patient Programmer, User Manual, purporting to bear a copyright date of 2008, 82 pages.
Medtronic, InterStim iCon® Model 3037 Patient Programmer, Quick reference guide, purporting to bear a copyright date of 2011, 2 pages.
Medtronic Interstim® Therapy, Test Stimulation Lead Kit and Test Stimulation Lead, Technical Manual, purporting to bear a copyright date of 2014, 26 pages.
Medtronic, Verify™ Evaluation System, Checking/ replacing batteries and reestablishing stimulation, purporting to bear a copyright date of 2014, 2 pages.
Medtronic, Verify™ Evaluation System for Sacral Neuromodulation, Advanced Evaluation Clinical Step Guide, purporting to bear a copyright date of 2014, 4 pages.
Medtronic, Verify™ Evaluation System, Technical Guide, purporting to bear a copyright date of 2014, 8 pages.
Medtronic, Verify™ External Neurostimulator for InterStim® Therapy, User Manual, purporting to bear a copyright date of 2014, 20 pages.
Medtronic, Verify™ External Neurostimulator for InterStim® Therapy, User Manual, purporting to bear a copyright date of 2015, 22 pages.
Advanced Bionics, Patient Trial Handbook, Precision Spinal Cord Stimulation System, purporting to bear a copyright date of 2006, 76 pages.
Advanced Bionics, Revolutionizing Spinal Cord Stimulation with the PRECISION™ SCS System, Precision Spinal Cord Stimulation System, purporting to bear a copyright date of 2005, 12 pages.
Boston Scientific, Precision™ System Clinician Manual, purporting to bear a copyright date of 2013, 86 pages.
Claim Chart for U.S. Pat. No. 10,589,103 for Precision™ System Clinician Manual dated Feb. 17, 2022, 27 pages.

* cited by examiner

EXTERNAL PULSE GENERATOR DEVICE AND ASSOCIATED METHODS FOR TRIAL NERVE STIMULATION

CROSS-REFERENCES TO RELATED APPLICATIONS

The present application is a continuation of U.S. Non-Provisional application Ser. No. 15/719,461 filed on Sep. 28, 2017, now U.S. Pat. No. 10,589,103, which is a continuation of U.S. Non-Provisional application Ser. No. 14/827,081 filed on Aug. 14, 2015, now U.S. Pat. No. 9,802,051, which claims the benefit of priority of U.S. Provisional Application No. 62/038,131 filed on Aug. 15, 2014; and 62/041,611 filed Aug. 25, 2014; the entire contents of which are incorporated herein by reference.

The present application is related to concurrently filed U.S. Non-Provisional patent application Ser. No. 14/827,074, now U.S. Pat. No. 9,802,038, entitled "Devices and Methods for Anchoring of Neurostimulation Leads"; Ser. No. 14/827,108, now U.S. Pat. No. 9,555,246, entitled "Electromyographic Lead Positioning and Stimulation Titration in a Nerve Stimulation System for Treatment of Overactive Bladder;" Ser. No. 14/827,095, now U.S. Pat. No. 10,092,762, entitled "Integrated Electromyographic Clinician Programmer For Use With an Implantable Neurostimulator'"; and Ser. No. 14/827,067, now U.S. Pat. No. 9,855,423, entitled "Systems and Methods for Neurostimulation Electrode Configurations Based on Neural Localization"; and U.S. Provisional Application Nos. 62/101,666, entitled "Patient Remote and Associated Methods of Use With a Nerve Stimulation System" filed on Jan. 9, 2015; 62/101,884, entitled "Attachment Devices and Associated Methods of Use With a Nerve Stimulation Charging Device" filed on Jan. 9, 2015; 62/101,782, entitled "Improved Antenna and Methods of Use For an Implantable Nerve Stimulator" filed on Jan. 9, 2015; and 62/191,134, entitled "Implantable Nerve Stimulator Having Internal Electronics Without ASIC and Methods of Use" filed on Jul. 10, 2015; each of which is assigned to the same assignee and incorporated herein by reference in its entirety for all purposes.

BACKGROUND OF THE INVENTION

Treatments with implanted neurostimulation systems have become increasingly more common in recent years. While such systems have shown promise in treating a number of chronic conditions, effectiveness of treatment may vary considerably between patients and viability of treatment can be difficult to determine before implantation. Although conventional methods of implantation often utilize preliminary testing with a temporary, partly implanted neurostimulation systems to assess viability of treatment, such systems may not provide an accurate representation of treatment with a fully implanted device. In addition, such systems are often bulky, uncomfortable and limit patient mobility, such that many patients elect not to receive a temporary system or a fully implanted system. In addition, many such temporary partly implanted systems may not operate in the same manner as their fully implanted counterparts due to differences between pulse generators or changes in position of the neurostimulation leads during conversion. Therefore, it is desirable to provide methods and devices for providing trial treatment systems that provide a more accurate representation of treatment, improve patient comfort and provide consistent treatment outcomes as compared to fully implanted neurostimulation systems.

BRIEF SUMMARY OF THE INVENTION

The present invention relates to neurostimulation treatment systems, and in particular a neurostimulation treatment having a partly implanted neurostimulation lead extending to an external pulse generator for conducting a trial neurostimulation treatment for assessing viability of a fully implanted system. In one aspect, the system includes a partly implanted neurostimulation lead that extends from one or more implanted neurostimulation electrodes to an external pulse generator (EPG) supported in an adherent patch affixed to the patient's skin. In certain embodiments, the EPG is sealed within a laminated flexible patch adhered to the patient so as to allow the patient to partake in normal everyday activities, including showering. The adherent patch may utilize a skin-compatible adhesive of sufficient strength to maintain adherence for the duration of the trial period. In some aspects, the trial period may be as little as 4-7 days, while in other aspects the trial period may extend two weeks or more, typically about four weeks. The system may further use additional adherent patches to seal the percutaneous incision through which the partly implanted lead extends and to maintain a position of the lead extending outside the body and prevent migration of the percutaneous portion of the lead. This is advantageous since often, during the trial period, the anchor portion of the lead may not be deployed so as to allow adjustment of the neurostimulation electrodes during the trial period.

In one aspect, a neurostimulation system includes an implantable neurostimulation lead having one or more conductors disposed within a lead body, the one or more conductors extending from a proximal end of the lead to one or more neurostimulation electrodes disposed at or near a distal end of the lead; an EPG electrically coupleable to the implantable lead, the pulse generator being electrically coupled with the one or more neurostimulation electrodes when electrically coupled with the implantable lead, wherein the pulse generator is configured to generate a plurality of electrical impulses for delivering a neurostimulation treatment to a patient through the one or more neurostimulation electrodes when implanted at a target location; and an adherent patch adapted to substantially cover the EPG and adhere to a skin of the patient so as to support the EPG on the skin of the patient for a duration of a trial period to assess efficacy of the neurostimulation treatment. The adherent patch comprises a flexible laminated patch, wherein the EPG is sealed within the laminated patch so as to be water resistant. The adherent patch includes a skin-compatible adhesive and material so as to be suitable for continuous adherence to the patient skin for the duration of the trial period, which can be anywhere from 4 days to 4 weeks or more.

In another aspect, the system may include a neurostimulation lead extension connected at one end to the proximal end of the implantable neurostimulation lead and coupleable with the EPG. The implantable neurostimulation lead is of a length suitable for implantation within a fully implanted neurostimulation system without removal of the distal portion from the target location after the trial period, wherein in the fully implanted neurostimulation system, the implantable pulse generator is implanted in a lower back region. The lead extension may be of sufficient length to position the EPG patch in a desired location, such a patient's abdomen. In one aspect, the lead extension may be coupled to the proximal end of the lead by a connector. The connector may operate in a similar manner as the interface on the IPG such that the lead can be disconnected from the lead extension and directly connected to the IPG during conversion to a permanent system.

In certain aspects, the EPG is a modified version of the IPG such that they operate in a similar manner in delivering electrical pulses to the neurostimulation pulses. The EPG is typically smaller and/or lighter than the implantable pulse generator such as by removing certain components of the IPG, such as replacing wireless charging coils and associated components of the IPG with a battery, or utilizing lighter, thinner housing materials such that the EPG is disposable. The EPG may be configured to be compatible with external control devices used with the IPG to allow easy transition between the devices during conversion to a permanently implanted system.

In another aspect, a neurostimulation system in accordance with aspect of the invention includes an implantable lead having one or more conductors disposed within a lead body, the one or more conductors extending from a proximal end of the lead to one or more neurostimulation electrodes disposed at or near a distal end of the lead; an EPG coupled to the proximal end of the implantable lead and sealed within an adherent patch attached to the patient, typically in a lower abdominal region. The EPG is configured to generate a plurality of electrical impulses to the implantable lead, the pulse generator being configured to generate a plurality of electrical impulses for delivering a neurostimulation treatment to a patient through the one or more neurostimulation electrodes when implanted at a target location; and an anchor coupled with the lead body just proximal of the electrodes.

In one aspect, the invention includes an anchoring body having a plurality of tines disposed along the anchoring body. The plurality of tines are biased toward a deployed position in which the tines extend laterally outward from the anchor body so as to engage tissue sufficiently to inhibit axial displacement of the implanted lead. The tines are constructed so as to be resiliently deflectable toward the helical body during implantation so as to fold inward toward the helical anchoring body when constrained by a delivery sheath to facilitate delivery to the target location during implantation. Typically, during the trial period, the sheath is disposed over the plurality of tines and the position of the neurostimulation lead is maintained by the additional adherent patches covering the portion of the lead extending outside the body to the EPG patch. This allows the lead position to be altered as needed during the trial to determine the most suitable lead position for treatment. If the trial proves successful, then the outer sheath can be withdrawn and the tines deployed so as to anchor the lead in position, after which the lead can be fully implanted along with an IPG. Methods of providing a trial treatment with such devices are also provided herein.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Neurostimulation has been used for many years to treat a variety of conditions, from chronic pain, to erectile dysfunction and various urinary dysfunctions. While neurostimulation has proven effective in many applications, effective therapy often relies on consistently delivering therapeutic activation by one or more neurostimulation electrodes to particular nerves or targeted regions with a pulse generator. In recent years, fully implantable neurostimulation have become increasingly more commonplace. Although such implantable systems provide patients with greater freedom and mobility, the neurostimulation electrodes of such systems are more difficult to adjust once they are implanted. The neurostimulation electrodes are typically provided on a distal end of an implantable lead that is advanced through a tunnel formed in a patient tissue.

Figure 1:
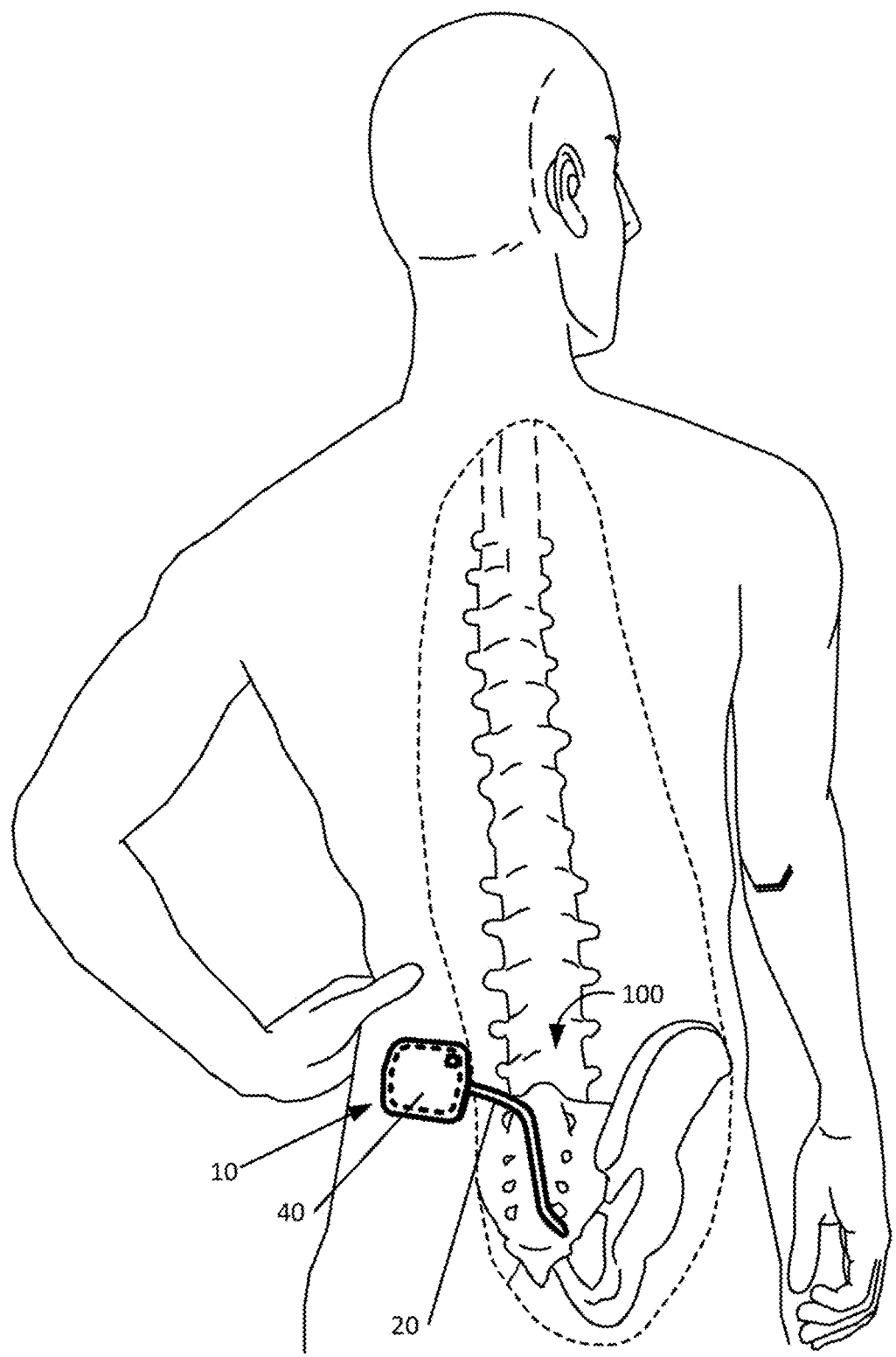
FIG. 1 is a schematic illustration of a trial neurostimulation system having a partly implanted lead extending to an EPG patch adhered to the skin of the patient, in accordance with aspects of the invention.

FIG. 1 schematically illustrates a use of a trial neurostimulation system utilizing an EPG patch, in accordance with aspect of the invention. Such a trial neurostimulation system can be used to assess viability of a fully implantable neurostimulation system. Implantable neurostimulation systems can be used in treating patients with, for example, chronic, severe, refractory neuropathic pain originating from peripheral nerves or various urinary and bowel dysfunctions. Implantable neurostimulation systems can be used to either stimulate a target peripheral nerve or the posterior epidural space of the spine. An implantable neurostimulation system includes an implanted pulse generator, typically implanted in a lower back region. In some embodiments, the pulse generator can generate one or more non-ablative electrical pulses that are delivered to a nerve to control pain or cause some other desired effect. In some applications, the pulses having a pulse amplitude of between 0-1,000 mA, 0-100 mA, 0-50 mA, 0-25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a microprocessor from Intel® or Advanced Micro Devices, Inc.®, or the like. An implantable pulse generator may implement an energy storage feature, such as one or more capacitors or a battery, and typically includes a wireless charging unit.

The electrical pulses generated by the pulse generator are delivered to one or more nerves and/or to a target location via one or more leads that include one or more neurostimulation electrodes at or near the distal end. The leads can have a variety of shapes, can be a variety of sizes, and can be made from a variety of materials, which size, shape, and materials can be dictated by the application or other factors. In some applications, the leads may be implanted to extend along the spine or through one of the foramen of the sacrum, such as shown in FIG. 1, such as in sacral nerve stimulation. In other applications, the leads may be implanted in a peripheral portion of the patient's body, such as in the arms or legs, and can be configured to deliver one or more electrical pulses to the peripheral nerve such as may be used to relieve chronic pain.

One or more properties of the electrical pulses can be controlled via a controller of the implanted pulse generator. In some embodiments, these properties can include, for example, the frequency, strength, pattern, duration, or other aspects of the timing and magnitude of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 1, the implantable neurostimulation system 100 includes a controller in the implantable pulse generator having one or more pulse programs, plans, or patterns and/or to select one or more of the created pulse programs, plans, or patterns.

Sacral nerve neuromodulation (SNM), also known as sacral nerve stimulation (SNS), is defined as the implantation of a permanent device that modulates the neural pathways controlling bladder or rectal function. This policy addresses use of SNM in the treatment of urinary or fecal incontinence, urinary or fecal nonobstructive retention, or chronic pelvic pain in patients with intact neural innervation of the bladder and/or rectum.

Treatment using SNM, also known as SNS, is one of several alternative modalities for patients with fecal or urinary incontinence (urge incontinence, significant symptoms of urgency-frequency, or nonobstructive urinary retention) who have failed behavioral (e.g., prompted voiding) and/or pharmacologic therapies. Urge incontinence is defined as leakage of urine when there is a strong urge to void. Urgency-frequency is an uncontrollable urge to urinate, resulting in very frequent, small volumes and is a prominent symptom of interstitial cystitis (also called bladder pain syndrome). Urinary retention is the inability to completely empty the bladder of urine. Fecal incontinence can result from a variety of mechanisms, including rectal wall compliance, neural pathways, nervous system, and voluntary and involuntary muscles. Incontinence is more common in women, often associated with muscular and neural damage that may occur during vaginal child delivery.

The SNM device consists of an implantable pulse generator that delivers controlled electrical impulses. This pulse generator is attached to wire leads that connect to the sacral nerves, most commonly the S3 nerve root. Two external components of the system help control the electrical stimulation. A patient remote control is kept by the patient and can be used to turn the device on or off or to adjust stimulation intensity. A console programmer is kept by the physician and used to adjust the settings of the pulse generator.

In a conventional approach, prior to implantation of the permanent device, patients undergo an initial testing phase to estimate potential response to treatment. The first type of testing developed was percutaneous nerve evaluation (PNE). This procedure is done under local anesthesia, using a test needle to identify the appropriate sacral nerve(s). Once identified, a temporary wire lead is inserted through the test needle and left in place for 4 to 7 days. This lead is connected to an external stimulator, which is carried by patients in their pocket or on their belt. The results of this test phase are used to determine whether patients are appropriate candidates for the permanent device. For example, for overactive bladder, if patients show a 50 percent or greater reduction in symptom frequency, they are deemed eligible for the permanent device.

The second type of testing is a 2-stage surgical procedure. In Stage 1, a quadripolar-tined lead is implanted (stage 1). The testing phase can last as long as several weeks, and if patients show a specified reduction in symptom frequency, they can proceed to Stage 2 of the surgery, which is permanent implantation of the neuromodulation device. The 2-stage surgical procedure has been used in various ways. These include its use instead of PNE, for patients who failed PNE, for patients with an inconclusive PNE, or for patients who had a successful PNE to further refine patient selection.

The permanent device is implanted under local or general anesthesia. An incision is made over the lower back and the electrical leads are placed in contact with the sacral nerve root(s). The wire leads are extended underneath the skin to a pocket incision where the pulse generator is inserted and connected to the wire leads. Following implantation, the physician programs the pulse generator to the optimal settings for that patient.

In the instance of bladder dysfunction, a trial period of sacral nerve neuromodulation with either percutaneous nerve stimulation or a temporarily implanted lead may be considered medically necessary (at least for purposed of insurance coverage) in patients that meet all of the following criteria: (1) a diagnosis of at least one of the following: urge incontinence; urgency-frequency syndrome; non-obstructive urinary retention; and overactive bladder, (2) there is documented failure or intolerance to at least two conventional therapies (e.g., behavioral training such as bladder training, prompted voiding, or pelvic muscle exercise training, pharmacologic treatment for at least a sufficient duration to fully assess its efficacy, and/or surgical corrective therapy); (3) the patient is an appropriate surgical candidate; and (4) incontinence is not related to a neurologic condition.

Permanent implantation of a sacral nerve neuromodulation device may be considered medically necessary in patients who meet all of the following criteria: (1) all of the criteria (1) through (4) in the previous paragraph are met; and (2) trial stimulation period demonstrates at least 50% improvement in symptoms over a period of at least one week.

Other urinary/voiding applications of sacral nerve neuromodulation are considered investigational, including but not limited to treatment of stress incontinence or urge incontinence due to a neurologic condition, e.g., detrusor hyperreflexia, multiple sclerosis, spinal cord injury, or other types of chronic voiding dysfunction. (See *policy description of sacral nerve neuromodulation/stimulation coverage provided by Blue Cross Blue Shield available online at*: http://www.bcbsms.com/com/bcbsms/apps/PolicySearch/views- NiewPolicy. php?&noprint=yes&path=%2Fpolicy %2Femed %2FSacral_Nerve_Stimulation.html)

Studies have shown that trial conversion rates, which is the rate at which patients convert a trial system to a permanently implanted system, are higher for Stage 1 trials than for PNE. For example, one study found that PNE trials resulted in a trial conversion rate of 40-50%, while Stage 1 trials resulted in 70-90% conversion, suggesting that Stage 1 generally provides a better indication of effectiveness of treatments. (See 1 Baster and Kim (2010). *Curr urol Rep*).

In another conventional approach, a similar method is used in peripheral neurostimulation (PNS) treatment systems. Generally, candidates for peripheral neurostimulation are assessed to determine their suitability for undergoing the PNS procedure. Prior to the surgery, the patient will undergo pre-surgical testing that includes routine blood tests as well as neuropsychological evaluation. The PNS procedure itself is typically performed in two separate stages. Each stage takes about one hour, and the patient can go home the same day.

In this aspect, Stage 1 involves implanting of trial electrodes, via small needles, which are connected to an external pulse generator (EPG), typically worn on a belt of the patient. A number of stimulation programs are administered over the next few days. If this trial demonstrates a significant improvement in the patient's headache or facial pain, permanent implantation can take place. In Stage 2, a new set of electrodes, the width of angel-hair pasta, are implanted under the skin. These are connected to a smaller implantable pulse generator implanted under the skin in the chest, abdomen, or back.

Among the drawbacks associated with these conventional approaches, is the discomfort associated with wearing an EPG, the risk of infection, as well as the additional procedures associated with removal of the implanted test leads and implantable of the permanent leads in Stage 2. In addition, often the EPG provided is different than the IPG that is eventually implanted. Given that efficacy of treatment often relies on precise placement of the neurostimulation electrodes at target tissue locations and consistent, repeatable delivery of neurostimulation therapy with the devices, the effectiveness of a trial period such as in PNE and Stage 1 trial periods are not always indicative of effective treatment with a permanent implanted system. In one aspect, since effectiveness of treatment in a trial period may rely, in part, on a patient's subjective experience, it is desirable if the discomfort and inconvenience of wearing an EPG by the patient can be minimized so that the patient can resume ordinary daily activities without constant awareness of the presence of the EPG and treatment system. This aspect can be of particular importance in treatment of urge-frequency, overactive bladder and erectile dysfunction, where a patient's awareness of the device could interfere with the patient's experience of symptoms associated with these conditions.

In one aspect, the invention allows for improved assessment of efficacy during trial periods by providing a trial system having improved patient comfort so that patients can more easily recognize the benefits and effectiveness of treatment. In another aspect, the trial system provides a better indication of effectiveness of treatment by utilizing the same implanted neurostimulation lead to deliver the therapy in the permanent system as was used to deliver the therapy in the trial system and further reduces the trauma associated with converting the trial system to the permanent system. In another aspect, the portions of the EPG delivering the therapy are substantially the same as the IPG in the permanent system such that the effects in permanent treatment should be more consistent with those seen in the trial system.

In certain embodiments, the invention provides an EPG patch worn on a skin of the patient so as to improve patient comfort. Optionally, the EPG used in Stage 1 may be smaller than the IPG used in the corresponding Stage 2 so that the EPG can easily be supported by and sealed against contamination by an adherent patch that covers the EPG. In one aspect, the EPG is a modified version of the implantable IPG used in Stage 2. The IPG may be modified by removal of one or more components, such as removal of a remote charging coil with a smaller battery and associated components. In addition, the EPG may use a thinner, lighter housing than the IPG, since the EPG is not required to last for many years, such as the IPG would be. The EPG therefore, may be configured to be disposable. These aspects allow the EPG to be supported within a patch worn on a skin of the patient at a convenient location, such as on the abdomen or side of the patient, as desired.

FIG. 1 illustrates an example trial neurostimulation system 100 having an EPG patch 10. As shown, the neurostimulation system is adapted to stimulate a ventral sacral nerve root. The neurostimulation system 100 includes an implantable pulse generator (IPG) implanted in a lower back region, from which a neurostimulation lead 20 extends through a foramen of the sacrum to electrodes (not shown) disposed near the sacral ventral root. The neurostimulation lead 20 further includes an anchor 10 disposed on a dorsal side of the sacrum. It is appreciated, however, that the anchor may be disposed on a ventral side of the sacrum as well, or within the foramen itself. In one aspect, the EPG 40 is disposable and discarded after the trial is complete. Typically, the trial may last anywhere from 4 days to 8 weeks. Typically, an initial assessment may be obtained after 4-7 days and, if needed, effectiveness of treatment may be examined after a few weeks, typically about 4 weeks. In one aspect, the EPG 40 of the EPG patch 10 is of a substantially similar design as the IPG that would be implanted if the trial proves successful, expect one or more components are removed to allow the EPG to be smaller in size and/or differing materials are used since the device may be intended for one time use.

Figure 2:
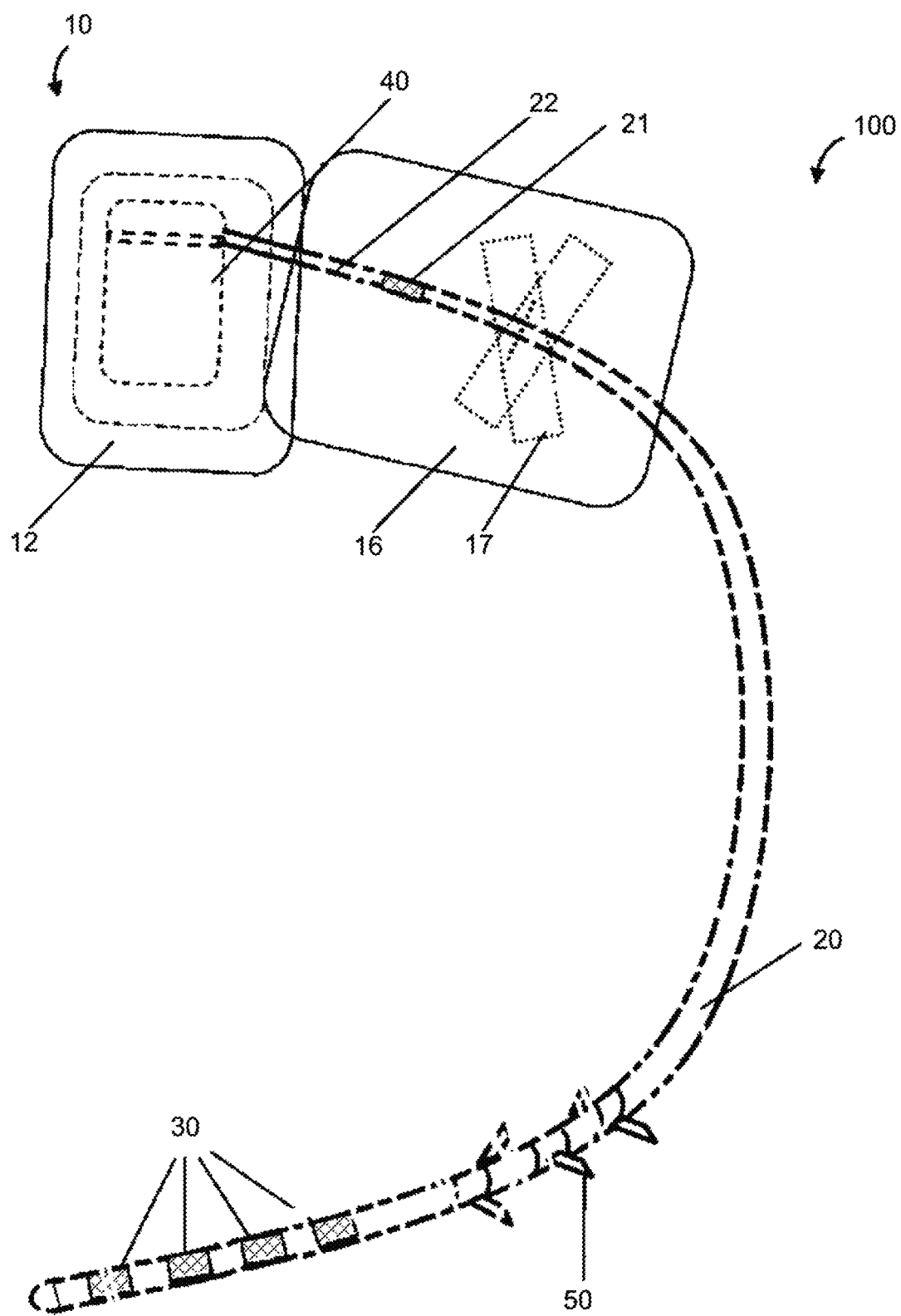
FIG. 2 is an overview of the neurostimulation system of FIG. 1.

FIG. 2 illustrates a neurostimulation system 100, similar to that in FIG. 1, in more detail. As can be seen, the neurostimulation lead 20 includes a plurality of neurostimulation electrodes 30 at a distal end of the lead and an anchor 50 having a plurality of tines disposed just proximal of the electrodes 30. Typically, the anchor is disposed near and proximal of the plurality of electrodes so as to provide anchoring of the lead relatively close to the electrodes. The EPG 40 is supported within an adherent patch 12 when attached to a skin of the patient. In one aspect, the EPG 40 used in the trial period is smaller than the corresponding IPG that would be implanted in a permanent system. This is made possible by removal of components that may not be necessary during a trial period or for an external device, for example the wireless charging coils and associated components. The EPG 40 may utilize a battery thereby allowing the device to be smaller and lighter so as to allow the EPG to be supported by an adherent patch and worn by a patient with minimal discomfort.

In one aspect, additional adherent patches 16 may be used to cover and seal the percutaneous incision in the skin of the patient through which the percutaneous portion of the neurostimulation lead is inserted. The lead may be secured at the percutaneous incision with surgical tape 17 and further secured and sealed with an adherent patch covering the lead and percutaneous incision. In this manner, the percutaneous incision can be sealed and protected from contamination or infection and its position maintained by the additional adherent patches 16. This configuration reduces the likelihood of infection and prevents movement of the lead, both internal and external, such that the patient's awareness of the patch and lead is minimized, thereby allowing the patient to resume relatively normal daily activities.

In another aspect, since the EPG patch may be worn in a different location, such as on the abdomen, than the IPG would be implanted, to allow the IPG to use the same percutaneous portion of the neurostimulation lead 20, the system may use a lead extension 22 coupled with the lead 20 by an external connector 21. The lead extension 22 may be hardwired into the EPG so as to eliminate potential disconnection and allow the connection to be sealed or encapsulated within the adherent patch so as to be water resistant or water proof. This allows the patient to perform routine daily activities, such as showering without removing the device. The length of lead 20 may be a suitable length for the permanently implanted system, while the length of extension 22 allows the lead to EPG patch to be positioned in a location that provide improved comfort and minimized interference with daily activities.

Figure 3:
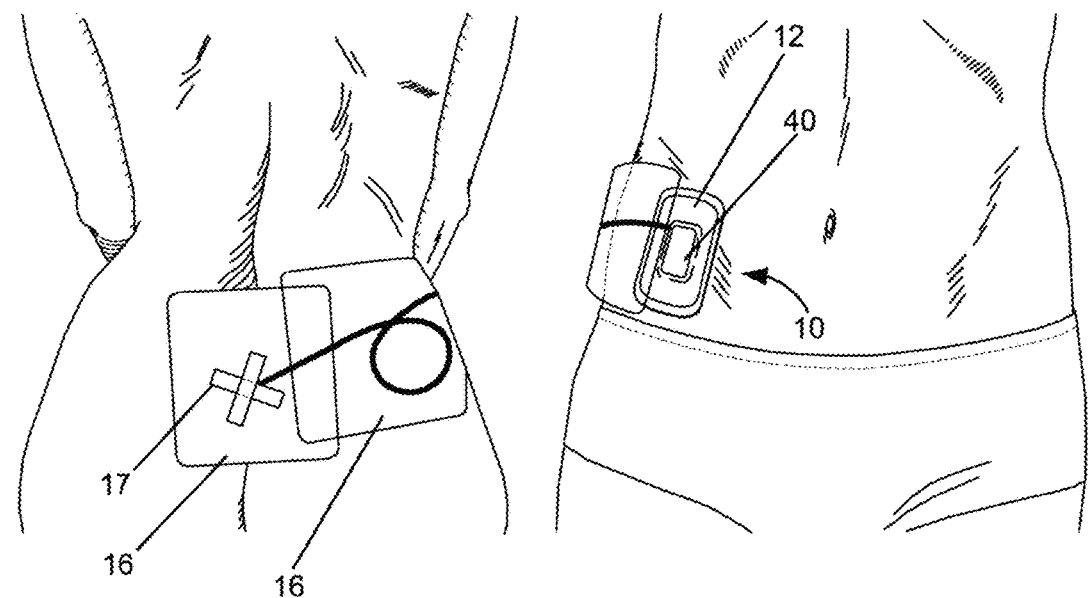
FIG. 3 is an alternative configuration of a trial neurostimulation system, in accordance with aspects of the invention.

FIG. 3 illustrates an alternate configuration in which the lead is sufficiently long to allow the EPG patch 10 to be adhered to the patient's abdomen. This configuration is advantageous as such placement allows the patient more mobility and freedom to resume daily activities and does not interfere with sitting or sleeping. Excess lead can be secured by an additional adherent patch 16, as shown by the center patch in FIG. 3. In one aspect, the lead is hardwired to the EPG, while in another the lead is removable connected to the EPG through a port or aperture in the top surface of the flexible patch 12. In one aspect, the EPG patch is disposable such that the lead can be disconnected and used in a permanently implanted system without removing the distal end of the lead from the target location. In another aspect, the entire system can be disposable and replaced with a lead and IPG.

In one aspect, the EPG unit may be wirelessly controlled by a patient remote in a similar or identical manner as the IPG of a permanently implanted system would be. The physician or patient may alter treatment provided by the EPG through use of a portable clinician unit and the treatments delivered are recorded on a memory of the device for use in determining a treatment suitable for use in a permanently implanted system.

Figure 4:
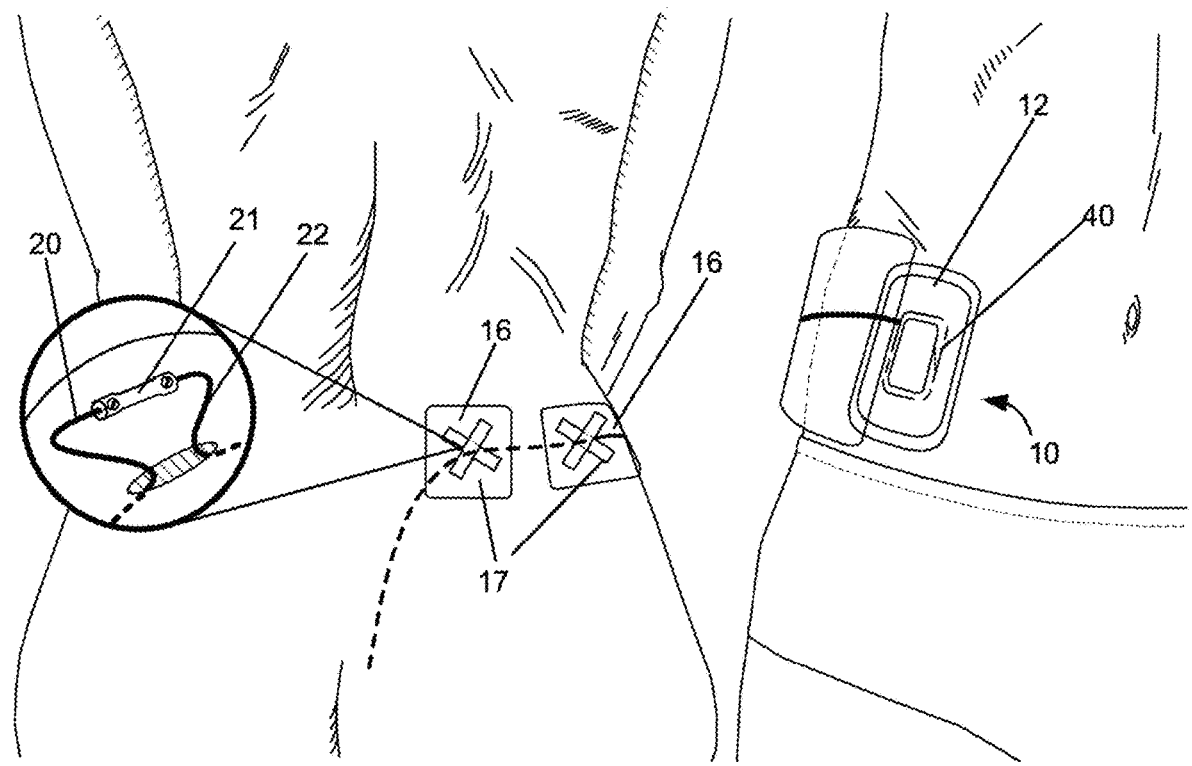
FIG. 4 is yet another alternative configuration of a trial neurostimulation system, in accordance with aspects of the invention.

FIG. 4 illustrates an alternate configuration in which the lead 20 is connected to a lead extension 21 through a connector 21. This allows the lead to be extended so that the EPG patch can be placed on the abdomen. This also allows the lead 20 of a length suitable for implantation in a permanent system to be used. This approach may utilize two percutaneous incisions, the connector 21 provided in the first incision and the lead extensions 12 extending through the second percutaneous incision, there being a short tunneling distance (about 10 cm) therebetween. This approach minimized movement of the implanted lead 20 during conversion of the trial system to a permanently implanted system. During conversion, the lead extension 22 can be removed along with the connector 21 and the implanted lead 20 attached to an IPG that is placed permanently implanted in a location at or near the site of the first percutaneous incision. In one aspect, the connector 21 may include a connector similar in design to the connector on the IPG. This allows the proximal end of the lead 20 to be coupled to the lead extension 22 through the connector 21 and easily detached and coupled to the IPG during conversion to a permanently implanted system.

Figure 5:
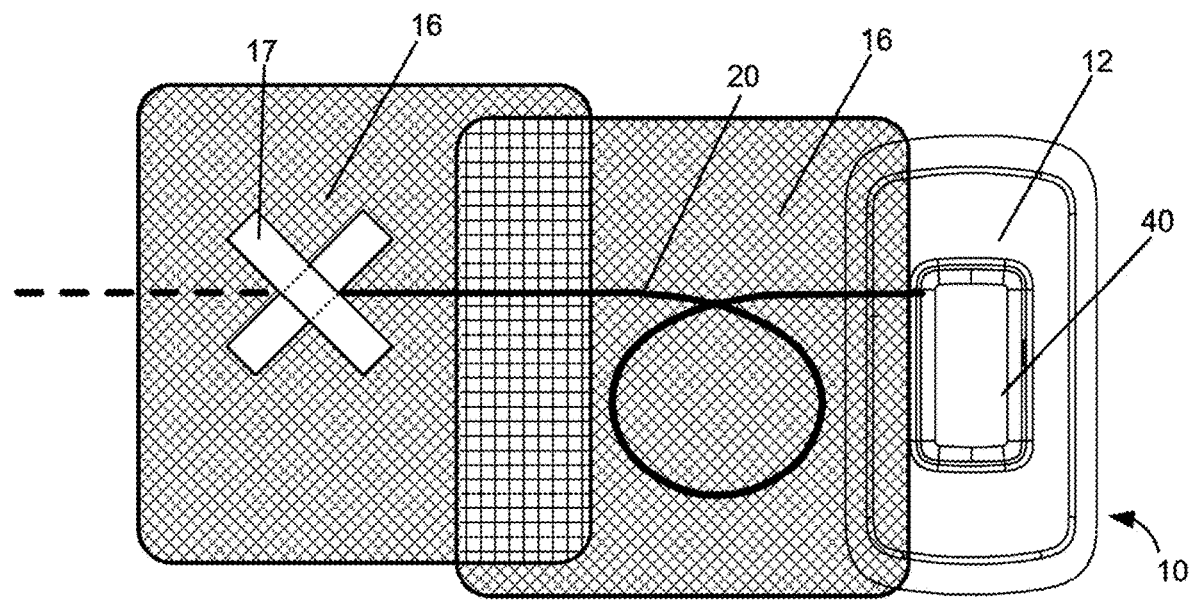
FIG. 5 is a detail of the neurostimulation system in FIG. 3.

FIG. 5 illustrates a detailed view of an EPG patch adhered to the skin of the patient, an additional adherent patch 16 disposed over the percutaneous incision through the lead extends into the patient and another additional patch 16 covering a loop of excess lead, the patch overlapping the first additional patch and the edge of the EPG patch 10. This configuration is advantageous as it substantially covers and seals the EPG and the lead from contamination and prevents accidental disconnection or migration of the lead by the patient, and streamlines the external portions of the system so as to improve patient comfort and allow a patient's subjective experience to more closely match what the patient would experience in a permanently implanted system.

Figure 6:
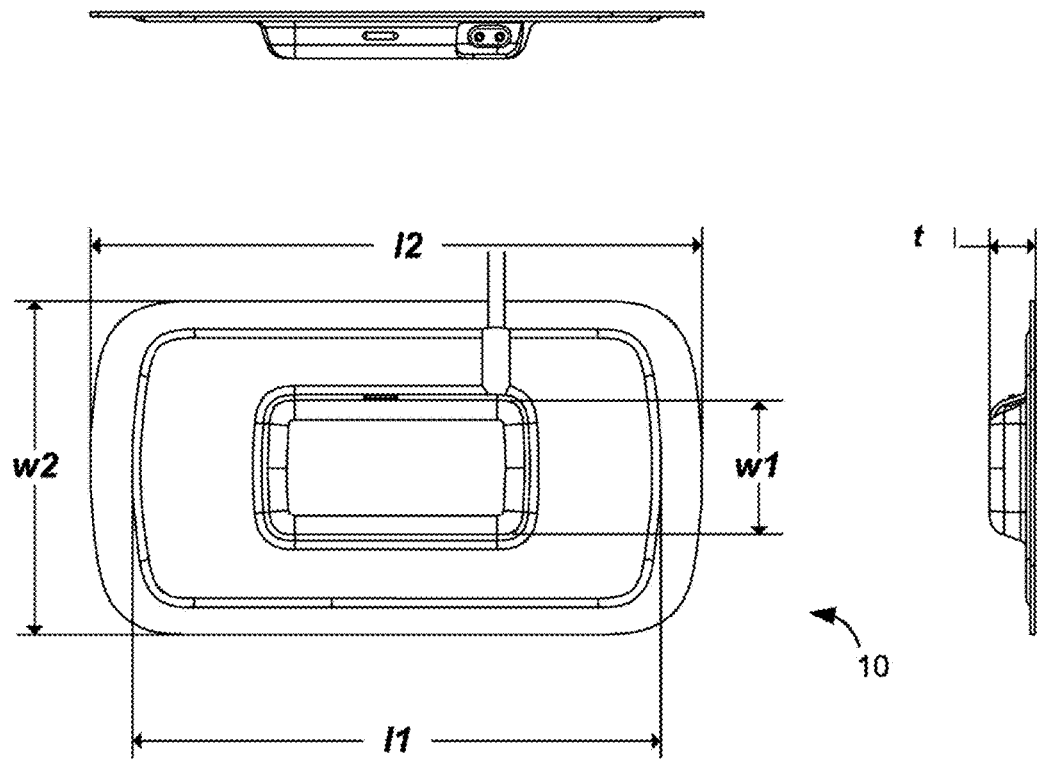
FIG. 6 is an overhead and side views of an example EPG patch, in accordance with aspect of the invention.

FIG. 6 illustrates an overhead view and side views of the EPG patch 10. In one aspect, the EPG is smaller than the IPG in the corresponding fully implantable permanent system. In certain embodiments, the outside width (w2) of the adherent patch 12 is between 2 and 5 inches, preferably about 2.5 inches, while the outside length (l2) of the patch 12 is between 3 and 6 inches, preferably about 4 inches; the width of the EPG (w1) is between 0.5 and 2 inches, preferably about 1 inch, while the length (l1) is between 1 and 3 inches, preferably about 2 inches; and the thickness (t) of the entire EPG patch 10 is less than 1 inches, preferably 0.8 inches or less. This design is considerably smaller than EPGs in conventional systems and thus interferes less with the daily activities of the patient during the trial period.

Figure 7A:
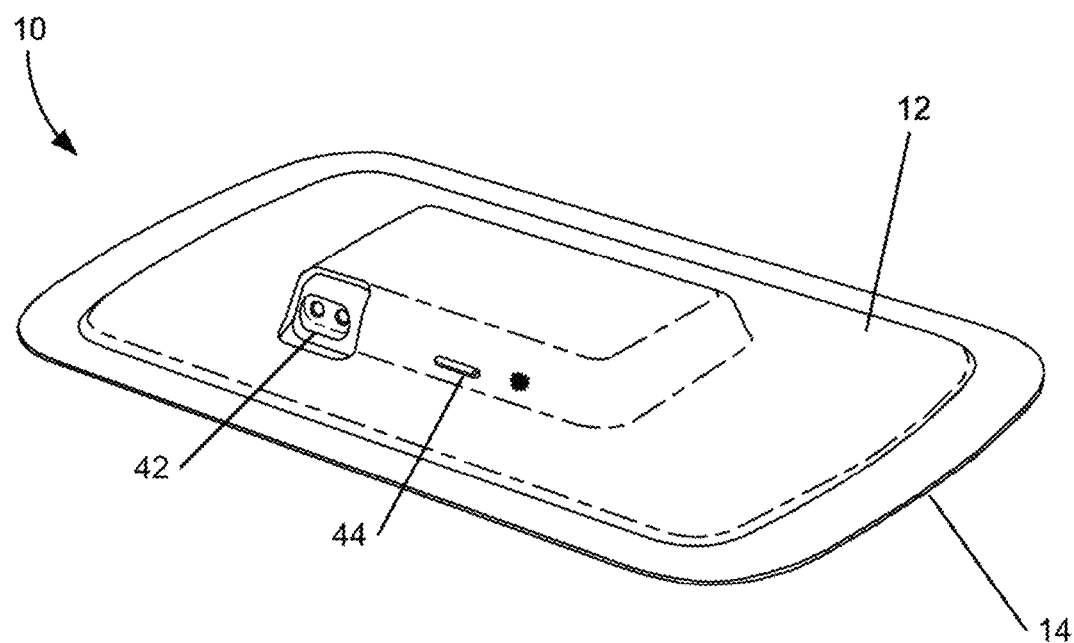
FIGS. 7A-7B illustrate an example EPG patch, in accordance with aspects of the invention.
Figure 7B:
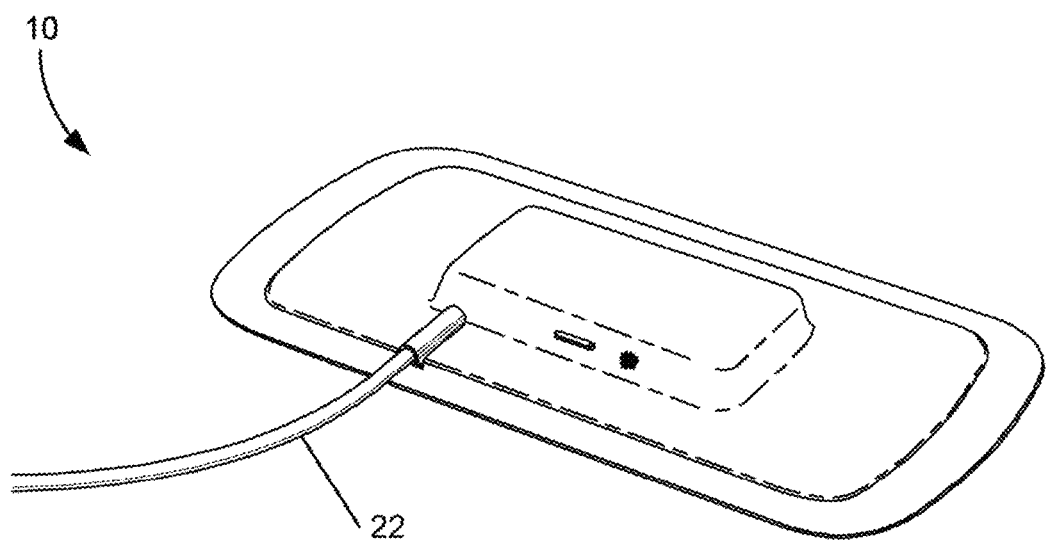

FIGS. 7A-7B illustrate perspective views of two example EPG patches 10. In FIG. 7A, the top surface of the flexible laminated patch 12 provides access to a connection port 42 of the EPG encased inside the patch. The patch may further include an "on/off" button 44 with a molded tactile detail to allow the patient to turn the EPG on and off through the outside surface of the adherent patch 12. The laminated surface of the patch 12 may also be partly transmissive to light such that an LED "on" indicator can be visible through the patch (the glow of the LED light can be seen to the right of the on/off button 44). The underside of the patch 14 is covered with a skin-compatible adhesive. The adhesive surface may be configured with any adhesive or adherent material suitable for continuous adhesion to a patient for the direction of the trial period. For example, a breathable strip having skin-compatible adhesive would allow the patch 12 to remain attached to the patient continuously for over a week, typically two weeks to four weeks, or even longer. In FIG. 7B, the EPG of the EPG patch is hardwired to the lead extension 22. This allows the entire lead extension 22 and EPG to be sealed, thereby improving the water resistance of the system. The advantages associated with embodiments of the EPG patch 10 described above include: disposability; increased patient mobility, including the ability to shower; improved patient comfort; lower infection of risk; and less tunneling through tissues required. These aspects increase the likelihood of trial period success and that patients will convert from the trial system to a permanently implanted system.

Figure 7C:
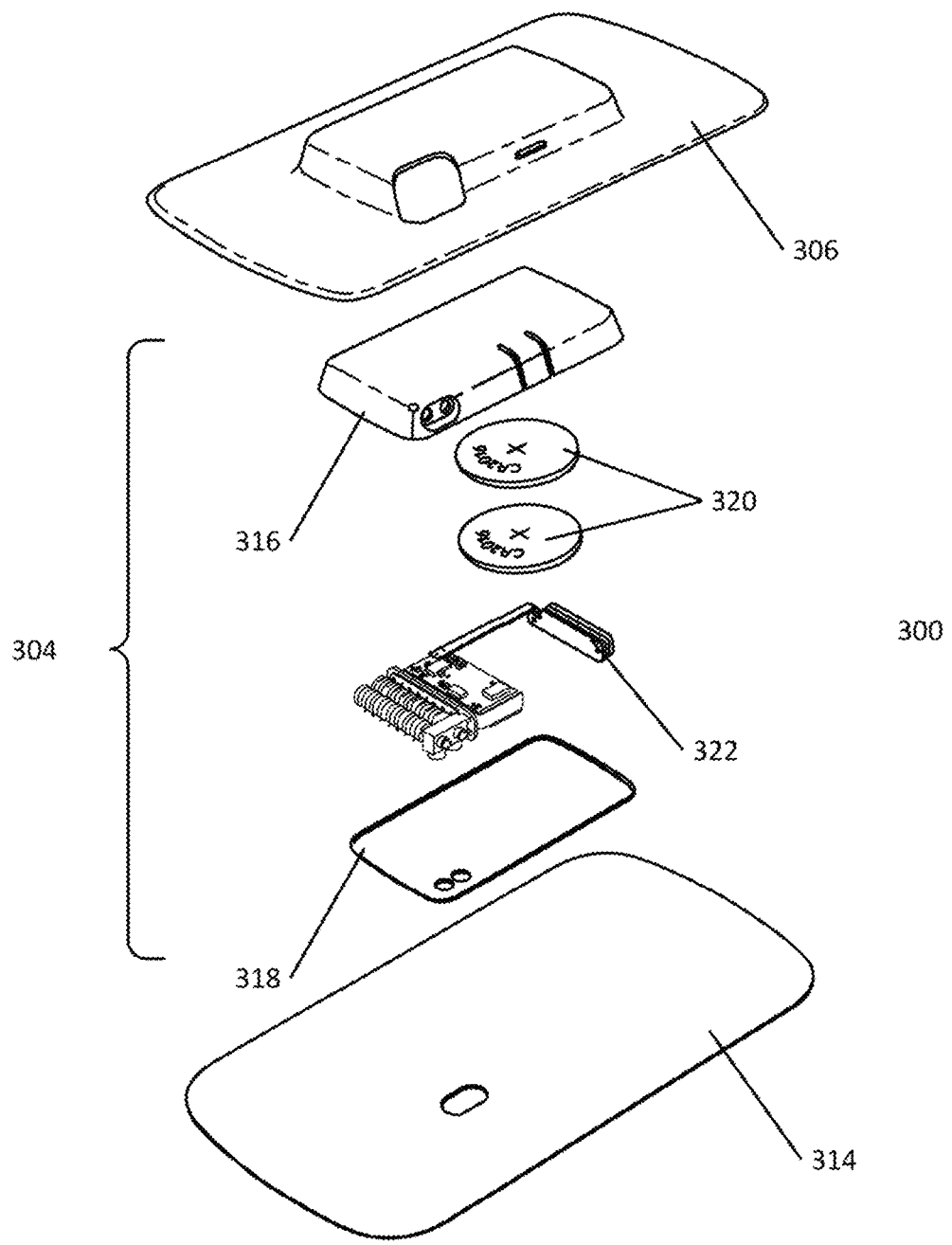
FIG. 7C is an exploded view illustration of an example EPG patch, in accordance with aspects of the invention.

FIG. 7C is an exploded view illustration of an example EPG patch 300. As illustrated, the EPG patch 300 can include a top surface of the patch 306 and a bottom surface of the patch 314 which can be bonded together to encase an EPG 304. Either or both of the top surface of the patch 306 and the bottom surface of the patch 314 can be replaceable and removable, such that both parts are removably bound to each other. The bottom surface of the patch 314 can further include a peel-off liner. The EPG 304 can be constructed of a thin plastic housing forming a shell, having a EPG shell top 316 and an EPG shell bottom 318. Within the shell of the EPG 304 one or more primary cells 320 can be contained, which individually or in combination can provide sufficient power for operation of the EPG 304 for about 14 days of use. Further, the EPG 304 can include internal circuitry 322 for generating pulses and other functionality.

Figure 8:
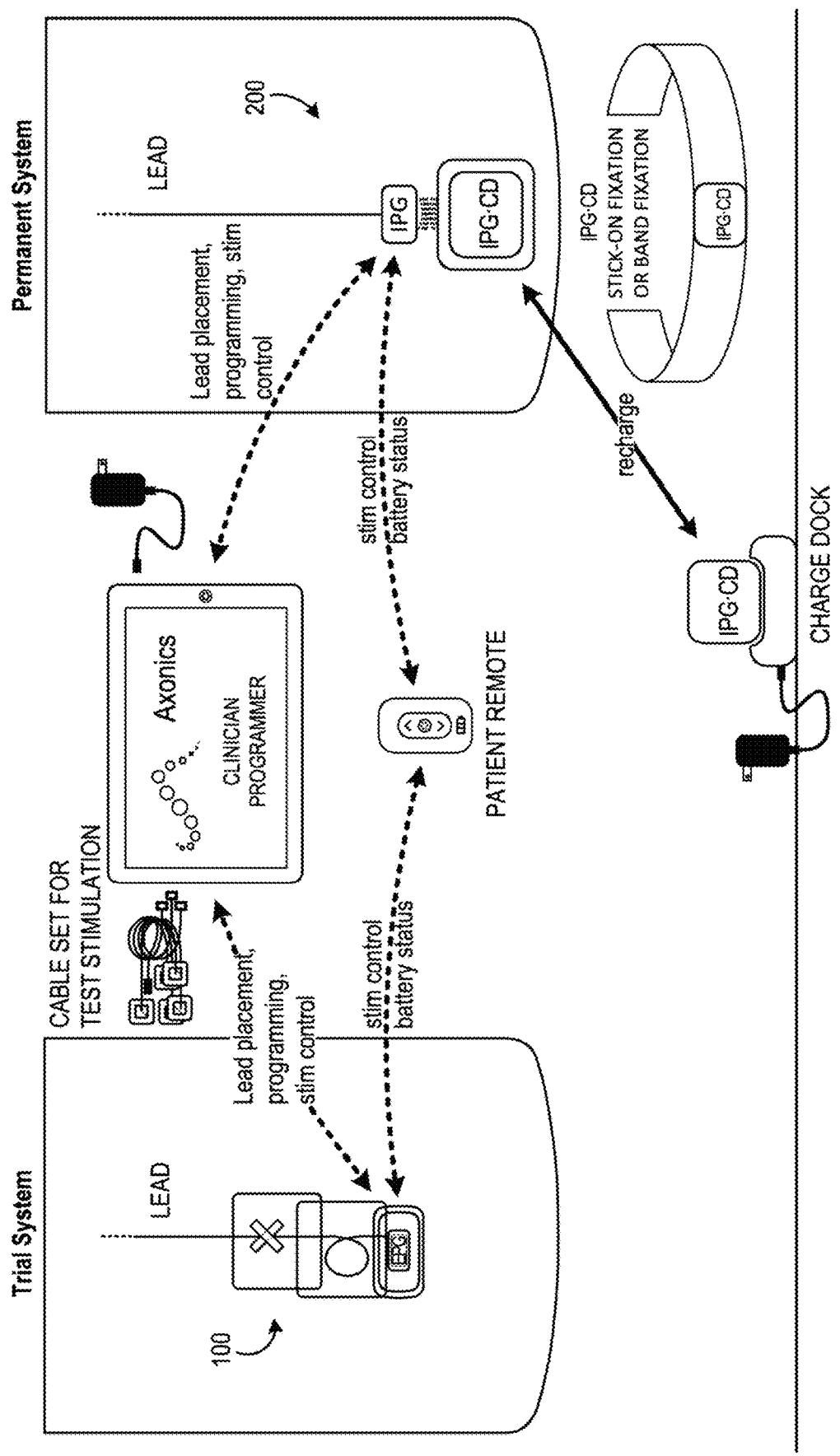
FIG. 8 schematically illustrates a use of a trial neurostimulation system utilizing an EPG patch, in accordance with aspect of the invention.

FIG. 8 illustrates a schematic of a trial system 100, in accordance with aspect of the invention, and a permanent system 200. As can be seen, each of the trial and permanent system are compatible for use with a wireless clinician programmer and a patient remote. The clinician programmer can be used in lead placement, programming and stimulation control in each of the trial and permanent systems. In addition, each allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system. The incremental increase or decrease of pulse generator stimulation level by the patient remote can be proportional to an existing or current stimulation level. In some embodiments, each incremental change will generally be more than 5% of existing stimulation or baseline stimulation, and can be ten percent (10%) of the existing stimulation level. For example, if a pulse generator is delivering treatment at a stimulation level of 2.0 mA, a single step up increasing the stimulation level can be 0.2 mA (10% of 2.0 mA), thereby increasing stimulation to 2.2 mA. A subsequent step up increasing the stimulation level can be 0.22 mA (10% of 2.2 mA), thereby increasing stimulation to 2.42 mA. Similarly, if a pulse generator is delivering treatment at a stimulation level of 4.0 mA, a single step down decreasing the stimulation level can be 0.4 mA (10% of 4.0 mA), thereby decreasing stimulation to 3.6 mA. In various embodiments, the step size by which the pulse generator stimulation level is changed can be 1% to 25% of the existing stimulation level, or any increment or gradient of a percentage within that range. The number of available treatment levels may be between 3 and 15, typically being between 4 and 10, and often being between 5 and 8.

Figure 9:
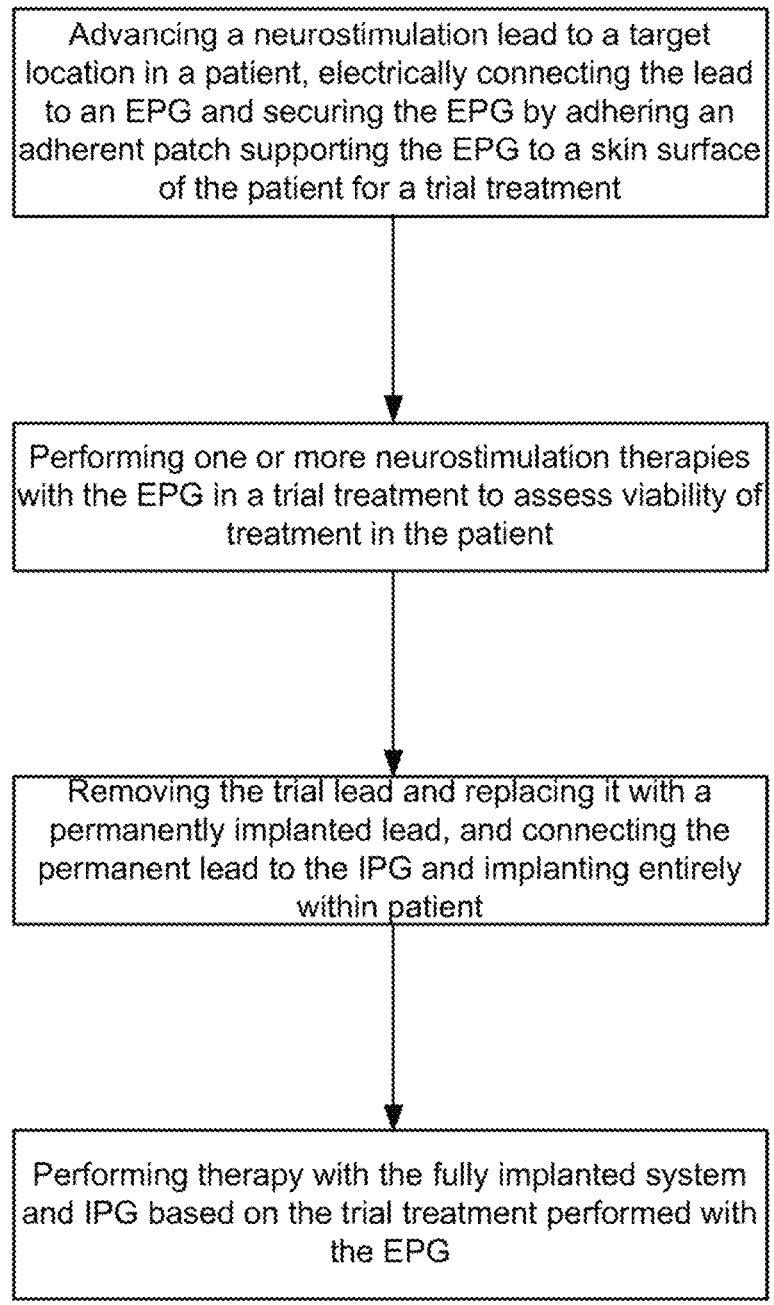
FIGS. 9-10 illustrate methods of performing a trial neurostimulation therapy in accordance with aspects of the invention.
Figure 10:
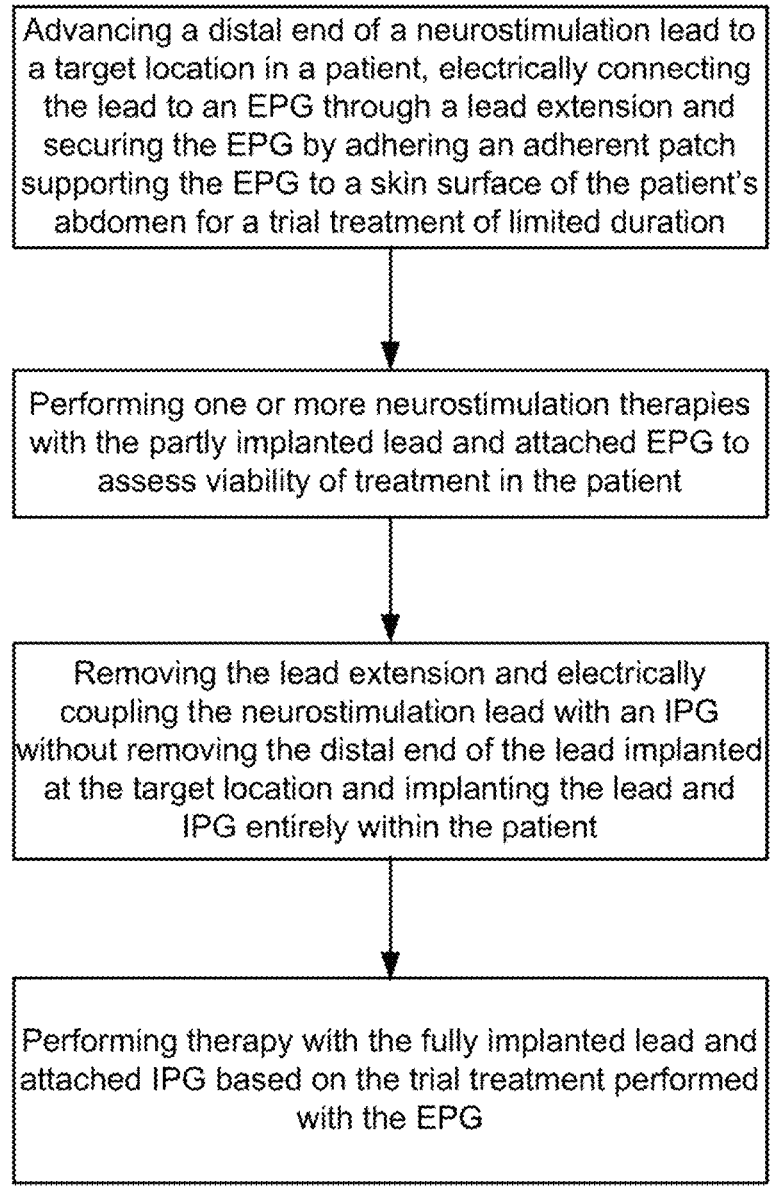

FIGS. 9-10 illustrate methods of treatment that may use an EPG patch in accordance with aspect of the invention. The method of FIG. 9 includes steps of: advancing a neurostimulation lead to a target location in a patient, electrically connecting the lead to an EPG and securing the EPG by adhering an adherent patch supporting the EPG to a skin surface of the patient (or optionally to securing the EPG to a belt worn by the patient) for a trial treatment; performing one or more neurostimulation therapies with the EPG in a trial treatment to assess viability of treatment in the patient; removing the implanted trial lead and replacing it with a permanently implanted lead, and connecting the permanent lead to the IPG and implanting the neurostimulation lead and IPG entirely within the body lead entirely within the patient; and performing therapy with the fully implanted system and IPG based on the trial treatment performed with the EPG.

The method of FIG. 10 includes steps of: advancing a distal end of a neurostimulation lead to a target location in a patient, electrically connecting the lead to an EPG through a lead extension and securing the EPG by adhering an adherent patch supporting the EPG to a skin surface of the patient's skin (or optionally to securing the EPG to a belt worn by the patient) for a trial treatment of limited duration; performing one or more trial neurostimulation therapies with the partly implanted lead and attached EPG to assess viability of treatment in the patient; removing the lead extension and electrically coupling the neurostimulation lead with an IPG without removing the distal end of the lead implanted at the target location and implanting the lead and IPG entirely within the patient; and performing therapy with the fully implanted lead and attached IPG based on the trial treatment performed with the EPG.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A neurostimulation pulse generator for delivering sacral neurostimulation therapy to a patient, the neurostimulation pulse generator comprising:
    a housing;
    circuitry disposed within the housing configured to:
        generate a plurality of electrical pulses for delivering a sacral neurostimulation treatment to a patient through one or more implanted neurostimulation electrodes coupled to the circuitry;
        couple the neurostimulation pulse generator with a patient remote, the patient remote being configured to control stimulation or monitor a battery status of the neurostimulation pulse generator; and
    a single user-interface element disposed on an exterior of the housing, the user-interface element
        being configured to turn the neurostimulation pulse generator ON or OFF;
    wherein the housing lacks manual stimulation adjustment controls disposed thereon;
    wherein the neurostimulation pulse generator is an external pulse generator configured to be disposable.

2. The neurostimulation pulse generator of claim 1, wherein the one or more implanted neurostimulation electrodes are coupled to the circuitry via one or more conductors of an implantable neurostimulation lead.

3. The neurostimulation pulse generator of claim 1, further comprising a battery power source configured to power the neurostimulation pulse generator for a duration of a trial period, wherein the duration of the trial period is at least one week.

4. The neurostimulation pulse generator of claim 1, further comprising a battery power source configured to power the neurostimulation pulse generator for a duration of a trial period, wherein the duration of the trial period is less than one week.

5. The neurostimulation pulse generator of claim 1, further comprising a lead extension electrically coupled to the circuitry.

6. The neurostimulation pulse generator of claim 5, wherein the lead extension is hardwired to the neurostimulation pulse generator.

7. The neurostimulation pulse generator of claim 5, wherein the lead extension is configured to be connected at one end to a proximal end of an implantable neurostimulation lead and coupleable at an opposite end to the neurostimulation pulse generator or an intervening connection.

8. The neurostimulation pulse generator of claim 1, wherein the circuitry is configured to couple the neurostimulation pulse generator with the patient remote wirelessly.

9. The neurostimulation pulse generator of claim 8, wherein the patient remote is further wirelessly coupleable with an implantable pulse generator, wherein the patient remote is configured to facilitate transition between a trial system and a permanent system, wherein the trial system corresponds to the external pulse generator and the permanent system corresponds to the implantable pulse generator.

10. The neurostimulation pulse generator of claim 9, further comprising a lead extension electrically coupled to the circuitry, wherein the lead extension is configured to be connected at one end to a proximal end of the implantable neurostimulation lead and coupleable at an opposite end to the external pulse generator or an intervening connection.

11. The neurostimulation pulse generator of claim 10, wherein the external pulse generator and the implantable pulse generator are further wirelessly coupleable to a clinician programmer, wherein the clinician programmer is configured to control programming and stimulation in each of the trial and permanent systems to facilitate transition between the trial system and the permanent system.

12. The neurostimulation pulse generator of claim 11, wherein the clinician programmer is configured to control stimulation and is further configured with additional programming functionality as compared to the patient remote.

13. The neurostimulation pulse generator of claim 10, wherein the external pulse generator includes a battery power source configured to power the external pulse generator and lacks any recharging coil and associated components for wireless charging.

14. The neurostimulation pulse generator of claim 8, wherein the patient remote is configured with a stimulation-increase button for increasing the stimulation level and a stimulation-decrease button for decreasing the stimulation level, wherein the patient remote is configured such that repeated actuation of the stimulation-increase button and stimulation-decrease button incrementally increases or decreases the stimulation level, respectively, by a step size that is 1% to 25% of an existing stimulation level or a baseline stimulation level.

15. A method of delivering a sacral neurostimulation treatment by stimulation of a sacral nerve, the method comprising:
implanting a distal end of a neurostimulation lead in a sacral nerve target location in a patient, the distal end of the neurostimulation lead having one or more neurostimulation electrodes;
electrically coupling the neurostimulation lead to a neurostimulation pulse generator, wherein the neurostimulation pulse generator is an external pulse generator that is configured to be disposable and includes a single user-interface element disposed on an exterior of a housing of the neurostimulation pulse generator, the user-interface element being configured to turn the neurostimulation pulse generator ON or OFF, and wherein a housing of the neurostimulation pulse generator lacks manual stimulation adjustment controls disposed thereon;
coupling the neurostimulation pulse generator with a patient remote, wherein the patient remote is configured to control stimulation or monitor a battery status of the neurostimulation pulse generator; and
performing one or more sacral neurostimulation treatments with the neurostimulation lead and the neurostimulation pulse generator.

16. The method of claim 15, further comprising adjusting stimulation settings via the patient remote.

17. The method of claim 15, further comprising:
implanting an implantable pulse generator and connecting to the neurostimulation lead implanted within the patient; and
coupling the patient remote with the implantable pulse generator, wherein the patient remote is configured to control stimulation or monitor a battery status of the implantable pulse generator in an identical manner as the external pulse generator.

18. The method of claim 17, wherein the patient remote is configured to facilitate transition from a trial system to a permanently implanted system, wherein the trial system corresponds to the external pulse generator and the permanently implanted system corresponds to the implantable pulse generator.

19. The method of claim 18, wherein electrically coupling the neurostimulation lead to the external pulse generator comprises attaching the external pulse generator and the neurostimulation lead via a lead extension, wherein the lead extension is configured to be connected at one end to a proximal end of the implantable neurostimulation lead and coupleable at an opposite end to the external pulse generator or an intervening connection.

20. The method of claim 19, wherein the external pulse generator and the implantable pulse generator are wirelessly coupled with the patient remote.

21. The method of claim 20, further comprising adjusting stimulation settings via the patient remote, wherein any adjusting of stimulation settings of the external pulse generator is performed by the patient after wirelessly coupling with the patient remote.

22. The method of claim 20, wherein performing the sacral neurostimulation treatment with the implantable pulse generator comprises communicating control instructions with a portable clinician programmer, wherein the control instructions are determined or selected based on the one or more sacral neurostimulation treatments performed with the external pulse generator.

23. The method of claim 22, wherein the external pulse generator and the implantable pulse generator are further wirelessly coupleable to the clinician programmer, wherein the clinician programmer is configured to control programming and stimulation in each of the trial and permanent systems to facilitate transition between the trial system and the permanent system.

24. The method of claim 20, further comprising:
powering the external pulse generator with an attached battery power source, the external pulse generator lacking any recharging coil and components for wireless charging; and
powering the implantable pulse generator with a power storage unit, the power storage unit being rechargeable through one or more wireless charging coils of the implantable pulse generator.

25. The method of claim 20, further comprising terminating the one or more sacral neurostimulation treatments performed with the external pulse generator in response to the single user-interface element being configured to turn the external pulse generator OFF.

26. The method of claim 15, wherein the one or more sacral neurostimulation treatments are performed during a trial period of at least one week.

27. The method of claim 15, wherein the one or more sacral neurostimulation treatments are performed during a trial period of less than one week.

28. The method of claim 15, wherein electrically coupling the neurostimulation lead to the neurostimulation pulse generator comprises attaching the neurostimulation pulse generator and the neurostimulation lead via a lead extension.

29. The method of claim 28, wherein the lead extension is hardwired to the neurostimulation pulse generator.

30. The method of claim 28, wherein the lead extension is configured to be connected at one end to a proximal end of the implantable neurostimulation lead and coupleable at an opposite end to the neurostimulation pulse generator or an intervening connection.

* * * * *